United States Patent
Jain et al.

(10) Patent No.: US 11,153,159 B2
(45) Date of Patent: Oct. 19, 2021

(54) DIGITAL THERAPEUTICS FOR PRECISION MEDICINE

(71) Applicant: Vignet Incorporated, Fairfax, VA (US)

(72) Inventors: Praduman Jain, Fairfax, VA (US); Dave Klein, Oakton, VA (US); Neeta Jain, Fairfax, VA (US); Yue Cao, Vienna, VA (US)

(73) Assignee: Vignet Incorporated, Fairfax, VA (US)

( * ) Notice: Subject to any disclaimer, the term of this patent is extended or adjusted under 35 U.S.C. 154(b) by 0 days.

(21) Appl. No.: 16/711,506

(22) Filed: Dec. 12, 2019

(65) Prior Publication Data
US 2020/0112479 A1   Apr. 9, 2020

Related U.S. Application Data

(63) Continuation of application No. 16/176,916, filed on Oct. 31, 2018, which is a continuation-in-part of
(Continued)

(51) Int. Cl.
*H04L 12/24* (2006.01)
*G16H 20/00* (2018.01)
(Continued)

(52) U.S. Cl.
CPC ......... *H04L 41/0813* (2013.01); *G06N 20/00* (2019.01); *G16H 20/00* (2018.01);
(Continued)

(58) Field of Classification Search
CPC ............ H04L 41/0813; H04L 41/0843; H04L 41/0853; H04L 12/24; H04L 12/26;
(Continued)

(56) References Cited

U.S. PATENT DOCUMENTS

| 6,039,688 A | 3/2000 | Douglas et al. |
| 6,260,022 B1 | 7/2001 | Brown |

(Continued)

FOREIGN PATENT DOCUMENTS

| EP | 2 545 468 | 3/1951 |
| WO | WO 2011/112556 | 9/2011 |

(Continued)

OTHER PUBLICATIONS

Torous J, Hsin H. Empowering the digital therapeutic relationship: virtual clinics for digital health interventions. NPJ digital medicine. May 16, 2018;1(1):1-3. (Year: 2018).*

(Continued)

*Primary Examiner* — James N Fiorillo
(74) *Attorney, Agent, or Firm* — Fish & Richardson P.C.

(57) ABSTRACT

Systems, methods, and devices, including computer-readable media, for managing operation of devices in complex systems and changing environments. In some implementations, a server system stores data indicating management plans for each of a plurality of different devices, each management plan indicating a device-specific set of program states for programs in a predetermined set of programs. The server system alters the management plans and enforces interdependence of the programs, and the server system generates a customized instruction that alters operation of the device according to the device-specific set of program states assigned in the altered management plan for the device. The server system causes each device to perform one or more operations of the device determined according to the device-specific set of program states assigned in the altered management plan for the device.

25 Claims, 12 Drawing Sheets

Related U.S. Application Data application No. 15/803,556, filed on Nov. 3, 2017, now Pat. No. 10,521,557.

(51) Int. Cl.

| | | |
|---|---|---|
| *H04L 29/08* | (2006.01) | |
| *G06N 20/00* | (2019.01) | |
| *G16H 40/67* | (2018.01) | |
| *G16H 50/20* | (2018.01) | |
| *G16H 40/40* | (2018.01) | |
| *G16H 40/20* | (2018.01) | |

(52) U.S. Cl.
CPC ............ *G16H 40/20* (2018.01); *G16H 40/40* (2018.01); *G16H 40/67* (2018.01); *G16H 50/20* (2018.01); *H04L 41/0843* (2013.01); *H04L 41/0853* (2013.01); *H04L 41/0893* (2013.01); *H04L 67/34* (2013.01)

(58) Field of Classification Search
CPC ..... H04L 41/08; H04L 41/0893; H04L 67/34; H04L 67/303; H04L 67/306; H04L 29/08; H04L 43/08; G06F 19/322; G06F 19/326; G06F 19/3418; G06F 19/3431; G06F 9/445; G06F 9/4419; G06F 9/44505; G06F 16/9535; G16H 40/20; G16H 40/40; G16H 40/67; G16H 20/00; G16H 50/20; G16N 20/00; G06N 3/04; G06N 3/08; G06N 3/0454
USPC .................................................. 709/206, 220
See application file for complete search history.

(56) References Cited

U.S. PATENT DOCUMENTS

| | | |
|---|---|---|
| 6,269,339 B1 | 7/2001 | Silver |
| 7,076,534 B1 | 7/2006 | Cleron et al. |
| 7,170,993 B2 | 1/2007 | Anderson et al. |
| 7,213,009 B2 | 5/2007 | Pstotnik et al. |
| 7,330,717 B2 | 2/2008 | Gidron et al. |
| 7,447,643 B1 | 11/2008 | Olson et al. |
| 7,730,063 B2 | 6/2010 | Eder |
| 8,583,453 B2 | 11/2013 | Plummer et al. |
| 8,589,175 B2 | 11/2013 | Glauser et al. |
| 8,684,922 B2 | 4/2014 | Tran |
| 8,706,521 B2 | 4/2014 | Ramarajan et al. |
| 8,707,392 B2 | 4/2014 | Birtwhistle et al. |
| 8,825,775 B2 | 9/2014 | Bohner et al. |
| 9,286,442 B2 | 3/2016 | Csoma et al. |
| 9,361,011 B1 | 6/2016 | Burns |
| 9,426,433 B1 | 8/2016 | Mazzarella |
| 9,461,972 B1 | 10/2016 | Mehta |
| 9,514,655 B1 | 12/2016 | Nusbaum et al. |
| 9,753,618 B1 | 9/2017 | Jain et al. |
| 9,844,725 B1 | 12/2017 | Durkin et al. |
| 9,848,061 B1 | 12/2017 | Jain et al. |
| 10,231,622 B2 | 3/2019 | Soyao et al. |
| 10,452,816 B2 | 10/2019 | Kidd et al. |
| 1,052,155 A1 | 12/2019 | Jain |
| 10,546,339 B2 | 1/2020 | Jiao et al. |
| 10,580,531 B2 | 3/2020 | Jiao et al. |
| 10,636,525 B2 | 4/2020 | Jiao et al. |
| 10,650,474 B2 | 5/2020 | Jiao et al. |
| 10,672,519 B2 | 6/2020 | Jiao et al. |
| 1,093,865 A1 | 3/2021 | Jain |
| 2001/0019338 A1 | 9/2001 | Roth |
| 2002/0010596 A1 | 1/2002 | Matory |
| 2002/0022973 A1 | 2/2002 | Sun |
| 2003/0165954 A1 | 9/2003 | Katagiri et al. |
| 2003/0182429 A1 | 9/2003 | Jagels |
| 2004/0030424 A1 | 2/2004 | Corl |
| 2004/0203755 A1 | 10/2004 | Brunet et al. |
| 2005/0086587 A1 | 4/2005 | Balz |
| 2005/0186550 A1 | 8/2005 | Gillani |
| 2005/0246304 A1 | 11/2005 | Knight et al. |
| 2006/0041452 A1 | 2/2006 | Kulkarni |
| 2006/0107219 A1 | 5/2006 | Ahya |
| 2006/0205564 A1 | 9/2006 | Peterson |
| 2007/0021984 A1 | 1/2007 | Brown |
| 2007/0172844 A1 | 7/2007 | Lancaster et al. |
| 2007/0231828 A1 | 10/2007 | Beachy et al. |
| 2007/0259351 A1 | 11/2007 | Chinitz et al. |
| 2007/0276270 A1 | 11/2007 | Tran |
| 2007/0281285 A1 | 12/2007 | Jayaweera |
| 2008/0005679 A1 | 1/2008 | Rimas-Ribikauskas |
| 2008/0127040 A1 | 5/2008 | Barcellona |
| 2008/0242221 A1 | 10/2008 | Shapiro et al. |
| 2008/0243038 A1 | 10/2008 | Bennett |
| 2008/0254429 A1 | 10/2008 | Woolf et al. |
| 2008/0261191 A1 | 10/2008 | Woolf et al. |
| 2008/0311968 A1 | 12/2008 | Hunter |
| 2009/0023555 A1 | 1/2009 | Raymond |
| 2009/0024944 A1 | 1/2009 | Louch |
| 2009/0031215 A1 | 1/2009 | Collier |
| 2009/0035733 A1 | 2/2009 | Meitar |
| 2009/0043689 A1 | 2/2009 | Yang |
| 2009/0076856 A1 | 3/2009 | Darby et al. |
| 2009/0125333 A1 | 5/2009 | Heywood |
| 2009/0163182 A1 | 6/2009 | Gatti |
| 2009/0170715 A1 | 7/2009 | Glinsky |
| 2009/0172002 A1 | 7/2009 | Bathiche |
| 2009/0276771 A1 | 11/2009 | Nickolov et al. |
| 2010/0041378 A1 | 2/2010 | Aceves |
| 2010/0082367 A1 | 4/2010 | Hains et al. |
| 2010/0179833 A1 | 7/2010 | Roizen et al. |
| 2010/0211941 A1 | 8/2010 | Roseborough |
| 2010/0250341 A1 | 9/2010 | Hauser |
| 2010/0262664 A1 | 10/2010 | Brown et al. |
| 2011/0173308 A1 | 7/2011 | Gutekunst |
| 2011/0184748 A1 | 7/2011 | Fierro et al. |
| 2011/0200979 A1 | 8/2011 | Benson |
| 2011/0230360 A1 | 9/2011 | Stephan et al. |
| 2012/0036220 A1 | 2/2012 | Dare et al. |
| 2012/0102050 A1 | 4/2012 | Button |
| 2012/0220835 A1 | 8/2012 | Chung |
| 2012/0266251 A1 | 10/2012 | Birtwhistle et al. |
| 2012/0272156 A1 | 10/2012 | Kerger |
| 2013/0060922 A1 | 3/2013 | Koponen et al. |
| 2013/0110565 A1 | 5/2013 | Means |
| 2013/0166494 A1 | 6/2013 | Davis |
| 2013/0238686 A1 | 9/2013 | O'Donoghue |
| 2013/0329632 A1 | 12/2013 | Buyukkoc et al. |
| 2014/0019191 A1 | 1/2014 | Mulji |
| 2014/0058755 A1* | 2/2014 | Macoviak ............... G16H 40/20 705/3 |
| 2014/0088995 A1 | 3/2014 | Damani |
| 2014/0100883 A1 | 4/2014 | Hamilton |
| 2014/0156823 A1 | 6/2014 | Liu |
| 2014/0181715 A1 | 6/2014 | Axelrod |
| 2014/0240122 A1 | 8/2014 | Roberts |
| 2014/0257058 A1 | 9/2014 | Clarysse et al. |
| 2014/0257852 A1* | 9/2014 | Walker .................. G16H 50/20 705/3 |
| 2014/0273913 A1 | 9/2014 | Michel |
| 2014/0278474 A1 | 9/2014 | McClure et al. |
| 2014/0297311 A1* | 10/2014 | Jackson ................ G16H 10/60 705/2 |
| 2015/0019342 A1 | 1/2015 | Gupta |
| 2015/0025917 A1 | 1/2015 | Stempora |
| 2015/0025997 A1 | 1/2015 | Tilenius et al. |
| 2015/0056589 A1 | 2/2015 | Zhang et al. |
| 2015/0135160 A1 | 5/2015 | Gauvin |
| 2015/0143470 A1 | 5/2015 | Stiekes et al. |
| 2015/0148061 A1 | 5/2015 | Koukoumidis |
| 2015/0199490 A1 | 7/2015 | Iancu et al. |
| 2015/0356701 A1 | 12/2015 | Gandy |
| 2016/0048652 A1 | 2/2016 | Spivey |
| 2016/0058287 A1 | 3/2016 | Dyell |
| 2016/0086505 A1 | 3/2016 | Hanlon |
| 2016/0189317 A1 | 6/2016 | Papandrea |
| 2017/0004260 A1* | 1/2017 | Moturu .................. G16H 50/20 |
| 2017/0011200 A1* | 1/2017 | Arshad .................. G16H 40/63 |

(56) References Cited

U.S. PATENT DOCUMENTS

| | | | |
|---|---|---|---|
| 2017/0020444 A1* | 1/2017 | Lurie | A61B 5/6898 |
| 2017/0124276 A1 | 5/2017 | Tee | |
| 2017/0132395 A1 | 5/2017 | Futch | |
| 2017/0235912 A1* | 8/2017 | Moturu | G16H 50/50 705/2 |
| 2017/0262606 A1* | 9/2017 | Abdullah | G06F 19/00 |
| 2017/0303187 A1 | 10/2017 | Crouthamel et al. | |
| 2017/0308669 A1 | 10/2017 | Apte et al. | |
| 2017/0323064 A1* | 11/2017 | Bates | A61B 5/7465 |
| 2017/0330297 A1 | 11/2017 | Cronin et al. | |
| 2018/0001184 A1 | 1/2018 | Tran et al. | |
| 2018/0025125 A1 | 1/2018 | Crane et al. | |
| 2018/0052971 A1* | 2/2018 | Hanina | A61B 5/4833 |
| 2018/0096740 A1 | 4/2018 | Moturu et al. | |
| 2018/0197624 A1 | 7/2018 | Robaina et al. | |
| 2018/0308569 A1 | 10/2018 | Luellen | |
| 2018/0365028 A1 | 12/2018 | Hosabettu | |
| 2019/0002982 A1 | 1/2019 | Wang | |
| 2019/0019581 A1* | 1/2019 | Vaughan | A61B 5/486 |
| 2019/0043501 A1 | 2/2019 | Ramaci | |
| 2019/0043610 A1* | 2/2019 | Vaughan | A61B 5/7267 |
| 2019/0043619 A1* | 2/2019 | Vaughan | G16H 20/10 |
| 2019/0074080 A1* | 3/2019 | Appelbaum | H04L 51/02 |
| 2019/0102670 A1* | 4/2019 | Ceulemans | G06F 21/6218 |
| 2019/0122266 A1 | 4/2019 | Ramer et al. | |
| 2019/0140892 A1 | 5/2019 | Jain et al. | |
| 2019/0147043 A1* | 5/2019 | Moskowitz | A61B 5/0531 704/9 |
| 2019/0172588 A1 | 6/2019 | Tran et al. | |
| 2019/0180862 A1 | 6/2019 | Wisser et al. | |
| 2019/0207814 A1 | 7/2019 | Jain et al. | |
| 2019/0214116 A1 | 7/2019 | Eberting | |
| 2019/0243944 A1 | 8/2019 | Jain et al. | |
| 2019/0286086 A1 | 9/2019 | Gardner et al. | |
| 2019/0313934 A1 | 10/2019 | Lee et al. | |
| 2019/0320310 A1 | 10/2019 | Horelik et al. | |
| 2020/0019995 A1* | 1/2020 | Krishnan | G06F 16/951 |
| 2020/0077942 A1* | 3/2020 | Youngblood | A61B 5/01 |
| 2020/0119986 A1 | 4/2020 | Jain et al. | |
| 2020/0135331 A1 | 4/2020 | Mohebbi | |
| 2020/0227152 A1 | 7/2020 | Moturu et al. | |
| 2021/0057091 A1 | 2/2021 | Gutekunst et al. | |

FOREIGN PATENT DOCUMENTS

| | | |
|---|---|---|
| WO | Wo 2016/161416 | 10/2016 |
| WO | WO 2017/106770 | 6/2017 |

OTHER PUBLICATIONS

U.S. Appl. No. 15/803,556, filed Nov. 3, 2017, Jain et al.

"Cancer Care Patient Navigation, a practical guide for community cancer centers," Association of Community Cancer Centers, 2009, [retrieved on Jan. 2, 2018], retrieved from: URL <https://www.accc-cancer.org/resources/pdf/Patient-Navigation-Guide.pdf>, 40 pages.

[No Author Listed] "Digital therapeutics," Wikipedia, Nov. 20, 2017, [retrieved on Jan. 2, 2018], retrieved from: URL <https://en.wikipedia.org/wiki/Digital_therapeutics>, 4 pages.

[No Author] "Methods for JITAIs Just in Time Adaptive Intervention," 2016, Nov. 9, 2016, [retreieved on Nov. 9, 2016], from the internet <https://community.isr.umich.edu/public/Default.aspx?alias=community.isr.umich.edu/public/jitai&>.

Braun et al., "Cancer Patient Navigator Tasks across the Cancer Care Continuum," J Health Care Poor Underserved, Feb. 1, 2012, 23(1):398-413.

Conner, "Experience sampling and ecological momentary assessment with mobile phones," 2015—http://www.otago.ac.nz/psychology/otago047475.pdf.

Farr, "Can "Digital Therapeutics" Be as Good as Drugs?," MIT Technology Review, Apr. 7, 2017, [retrieved on Jan. 2, 2018], retrieved from: URL <https://www.technologyreview.com/s/604053/can-digital-therapeutics-be-as-good-as-drugs/>, 8 pages.

Heron, "Ecological Momentary Intervention [EMI]: Incorporating mobile technology into a disordered eating treatment program for college women," Psychology—Dissertations, paper 157, 2011.

http://www.khanacademic.org, 2017, 1 page.

Milward, "Ecological momentary assessment," Jul. 2015, [retrieved on May 12, 2017], from the internet <https://www.addiction-ssa.org/commentary/emerging-research-methods-series-ecological-momentary-assessment>, 3 pages.

Runyan et al., "Virtues, ecological momentary assessent/intervention and smartphone technology," Front Psychol, 2015;6:481.

Shockney, "The Value of Patient Navigators as Members of the Multidisciplinary Oncology Care Team," 2017 ASCO Annual Meeting, ASCO Daily News, Jun. 6, 2016, [retrieved on Jan. 2, 2018], retrieved from: URL <https://am.asco.org/value-patient-navigators-members-multidisciplinary-oncology-care-team>, 3 pages.

Simon, "Patient Navigators Help Cancer Patients Manager Care," American Cancer Society, Feb. 24, 2017, [retrieved on Jan. 2, 2018], retrieved from: URL <https://www.cancer.org/latest-news/navigators-help-cancer-patients-manage-their-care.html>, 4 pages.

Teems, "Automated Patient Navigation: Commission on Cancer and Other Requirements," Cordata Healthcare Innovations; Cordata Blog, Oct. 13, 2014, [retrieved on Jan. 2, 2018], retrieved from: URL <http://www.cordatahealth.com/blog/automated-patient-navigation-commission-on-cancer-and-other-requirements>, 4 pages.

USPTO Non-Final Office Action in U.S. Appl. No. 15/803,556, dated Nov. 26, 2018, 22 pages.

USPTO Final Office Action in U.S. Appl. No. 15/803,556, dated Jun. 6, 2018, 23 pages.

USPTO Non-Final Office Action in U.S. Appl. No. 15/803,556, dated Jan. 2, 2018, 23 pages.

USPTO Non-Final Office Action in U.S. Appl. No. 16/176,916, dated Feb. 5, 2020, 53 pages.

USPTO Notice of Allowance in U.S. Appl. No. 15/803,556, dated Aug. 2, 2019, 10 pages.

USPTO Non-Final Office Action in U.S. Appl. No. 16/711,498, dated Mar. 11, 2020, 42 pages.

Boulos et al., "How smartphones are changing the face of mobile and participatory healthcare: An overview, with example from eCAALYX", Biomedical Engineering Online, Dec. 2011, 10(10:24.

USPTO Advisory Action in U.S. Appl. No. 16/176,916, dated Sep. 11, 2020, 7 pages.

USPTO Final Office Action in U.S. Appl. No. 16/176,916, dated Aug. 4, 2020, 43 pages.

USPTO Final Office Action in U.S. Appl. No. 16/711,498, dated Sep. 11, 2020, 55 pages.

USPTO Notice of Allowance in U.S. Appl. No. 16/711,498, dated Dec. 30, 2020, 25 pages.

* cited by examiner

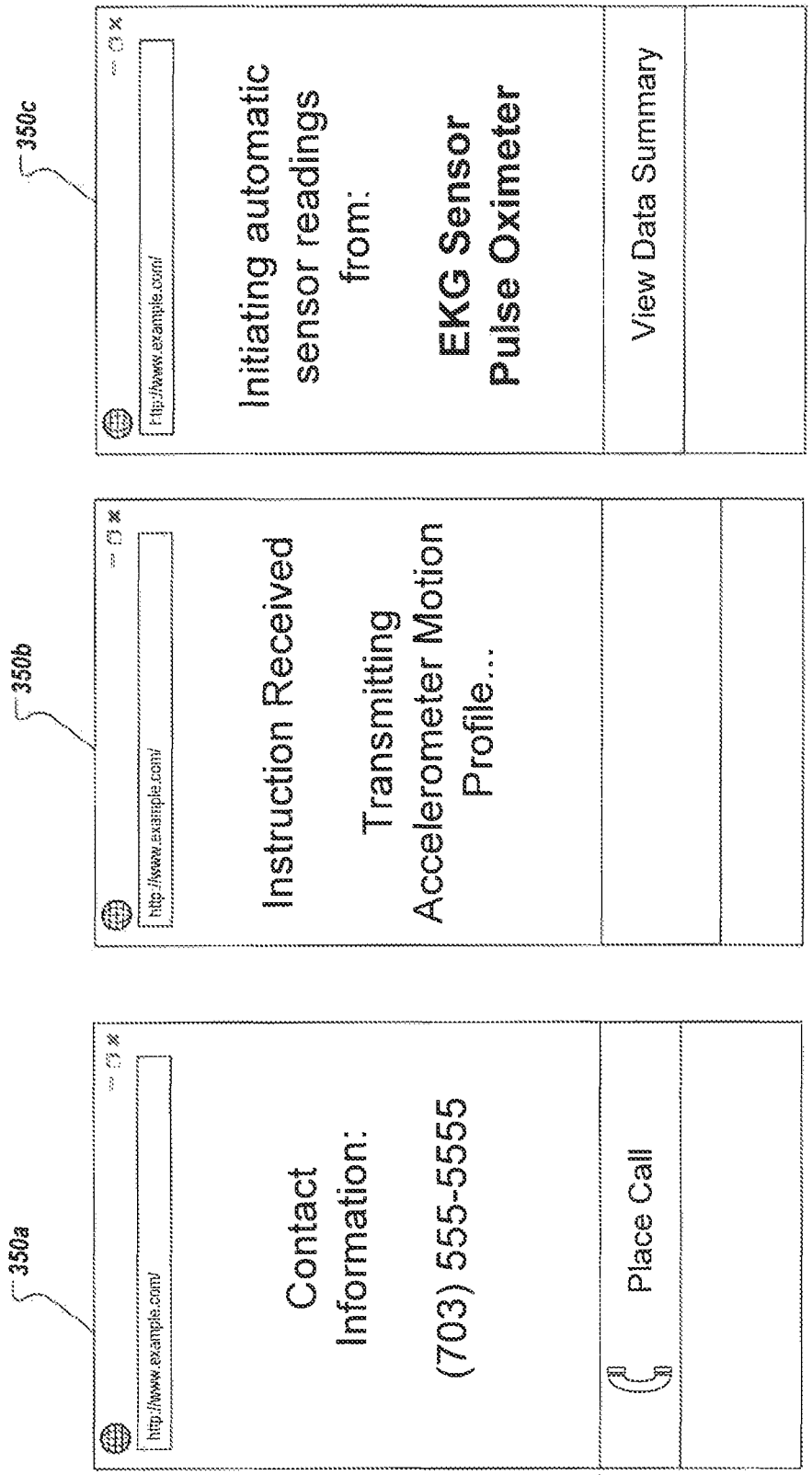

| Device Name | Days in Program | Operating Characteristics | Program ID | Attention Required |
|---|---|---|---|---|
| Device 1 | 3 | poor randomization, poor battery life | 0336410 | |
| Device 2 | 45 | poor battery life | 9102338 | ✓ |
| Device 3 | 12 | inaccurate GPS, inaccurate color reproduction | 641883a | |
| Device 4 | 89 | poor battery life | 9102338 | |

FIG. 3E

DIGITAL THERAPEUTICS FOR PRECISION MEDICINE

CROSS-REFERENCE TO RELATED APPLICATIONS

This application is a continuation of U.S. patent application Ser. No. 16/176,916, filed on Oct. 31, 2018, which is a continuation-in-part of U.S. patent application Ser. No. 15/803,556, filed on Nov. 3, 2017. The entirety of both of the prior applications is incorporated by reference herein.

TECHNICAL FIELD

This document generally relates to computing techniques that can be used to efficiently manage networked devices, including making fine-grained context-dependent adjustments to the operation of devices in complex and/or distributed systems.

BACKGROUND

Management of devices in complex systems can be challenging. In many cases, equipment is managed using manual intervention and determinations, for example, repairing devices when components fail. Although many devices of similar capabilities may be employed, the physical state of each device may be unique (e.g., maintenance status, component status, battery life, etc.) and the context and tasks of each device may also be unique and variable. Yet devices of a similar type are often controlled in the same manner regardless of varying physical state and context, often with detrimental long-term results. When a portion of a system malfunctions or needs repair, a significant section or even the entire system may be affected. For example, in a manufacturing environment, a first machine's failure or poor quality output may result in waste or in idling of many other machines that require the first machine's output to perform their tasks properly.

SUMMARY

In some implementations, a system creates and manages dynamic, customized plans for managing networked devices in complex systems, including networked devices that may or may not interact directly with users. The system can coordinate operating programs that affect different operational characteristics, including changes to alter wear, output, interactions, risks, and user-facing behavior. The dynamic operating programs allow the system to interact with various other systems to automatically adjust the content of each management plan. The system also carries out the plans by issuing real-time commands. The system can react to each device's current situation with contextually relevant changes to the device's management plan. The interactions of the system are not limited to the device. The system can also interact with other devices that are connected to (e.g., in communication with) or related to the device, such as devices of plant managers, maintenance workers, or other users. The system can also assess unique risk levels for each device and predictively act to mitigate those risks. Further, the system can use machine learning techniques to identify the combinations of interventions that best improve outcomes for different devices or groups of devices.

One of the advantages of the system is the ability to use a common set of digital operating programs to provide unique, adaptive, customized instructions for a wide variety of complex systems. The system may also provide real-time or near-real-time responsiveness to adjust for a device's current status and situation.

In general, maintaining and updating sophisticated software can be difficult, especially as computer systems and requirements change over time. A particular challenge is managing the dependency among different elements of a system. Traditional systems often require static dependency among software components or impose other constraints on relationships between modules, and changes to one component often require updates to many other related components to accommodate the changes. Some systems may use independent components, but with significantly less flexibility and greater overhead, since the components may not effectively share information.

The present application describes solutions to the inflexibility and inefficiency of many software platforms with a new technique to address dependency among sophisticated software systems and vary management plans with low overhead. In some implementations, the system uses a collection of modules or programs hosted by a server system. The same set of modules or programs are used together for the creation, carrying out, and ongoing adaptation of management plans for many different devices, yet the content of the programs and interrelationships allow for vast numbers of unique management plans through different combinations and settings for the programs. The programs can operate in parallel and asynchronously to each other, and can share the same data sets to reduce storage requirements and overhead. As discussed further below, each program may be capable of operating at any of multiple different states, where each program state corresponds to different behavior of the program, e.g., using different sets of rules for device actions and different sets of interactive content. The set of programs can, collectively and in different combinations, address the unique needs and circumstances of many different devices, with the system using a device-specific or user-specific set of program states for each device that it manages. For example, if a system has three programs, each with states 1-10, a first device may be supported with the programs at states 1, 3, and 2, a second device may be supported by the same programs operating at states 2, 3, and 5, and so on. The programs can also use common data sets (e.g., rule sets, content repositories, control parameters such as thresholds, etc.) for each device, which are available to all programs, to minimize storage requirements and latency.

The programs can be designed to operate in any of the given program states without dependency on any of the other programs, so that operation or delay of any program does not block operation of other programs. Nevertheless, the system enables interdependence among the programs in the manner that the program states are set. For example, the system can dynamically set the program states of programs for a device according to the program states of other programs for the same device. For example, although each program can represent a self-contained unit that can operate and interact with devices separate from other programs, the system may also take into account a device's user-specific program states for all programs when the system evaluates whether to dynamically change program states. Based on the state of one program, the system may determine to change the state of other programs, to achieve an appropriate combination of programs active at any given time for a particular user. The changes in program state can be made periodically and asynchronously, so that other programs can continue in their current states or change states as needed.

In addition, by sharing the same programs and discrete states of those programs for many devices, the system can provide many different combinations of experiences with a small number of programs and states. This maximizes the ability of the system to customize interaction and adapt for individual devices or users, while minimizing storage requirements and effort to maintain the system. For example, a system that uses ten programs with ten states each has a total of 100 individual program states, but provides $10^{10}$ or 10 billion different combinations of program states, where each combination can provide a different management plan. This allows a very large level of flexibility and customizability with high efficiency, e.g., small storage space and minimal computation for the scope of variability allowed. Further, for each combination of program states, the operation of the programs (e.g., application of the subset of rules corresponding to the applicable program states) further customizes interaction with the device according to a current context, history of interactions, and other data specific to a particular device or its user.

In some implementations, the system includes multiple digital operating programs that each relate to a different aspect of the device's operation or a user's needs. Each program can have a corresponding set of rules that specify system actions to be performed when appropriate triggers and conditions are satisfied. The system can also use the output of these programs and the state of the programs to adjust the nature of the user's management plan. The various programs can be interdependent, with different programs having states that are modified by the system based at least in part on the state of other programs. In this manner, programs that are not directly related in topic or function to other programs can nevertheless affect each other's state (e.g., whether the program is activated, and at what level or intensity). The manner in which these programs interact (e.g., how programs and conditions trigger adjustments in other programs) can be learned by the system through machine learning techniques.

The device management technique described in the present specification provides various advantages over existing management techniques. For example, the present method allows individualized management for each device, which can have unique operating characteristics, which can avoid or mitigate the need for maintenance by proactively and dynamically adjusting operation according to the devices unique context and state.

Because the operating characteristics of a device may be interrelated or may combine during certain tasks or activities, and a change to one operating characteristic of a device can affect or induce a change in a different operating characteristic, the device management plan can account for changes to a particular operating characteristic by changing levels of a particular program in response to changes to an operating characteristic.

The generation of management plans can be performed by a user, automatically, or as a combination (e.g., automatically with input from a user). For example, a management plan can be generated using a set of programmed guidelines, with certain variables that can be input by a user. In some examples, the management plans can be generated automatically through the application of machine learning techniques. For example, operational data of devices in a similar context or situation can be collected over time, and trends and patterns observed can be used as training examples use to determine the training state of a classifier, neural network, or other machine learning model, which can learn to indicate combinations of program states that are appropriate for different situations.

The management method can be applied to other complex systems, such as network-connected devices in distributed environments. Some figures and description below refer to devices in a factory for ease and simplicity of explanation. The same techniques are also applicable in a wide variety of other settings, such as telecommunications, managing robots or autonomous vehicles, providing digital therapeutics or precision medicine, and so on.

In one general aspect, a system includes one or more computers of a server system, the one or more computers being configured to carry out and update management plans that adjust operation of one or more devices, where the management plans involve different combinations of programs in a predetermined plurality of programs, each of the programs having multiple predetermined program states specifying different levels of interaction or different levels of intensity of the corresponding program. The server system includes a data storage subsystem configured to store data indicating a management plan for a device, the management plan indicating a device-specific set of program states for the plurality of programs. The server system includes a program state setting module configured to alter the management plan for the device by assigning, in the altered management plan, an altered device-specific set of program states corresponding to the plurality of programs, where the program state setting module enforces interdependence among the programs such that the program states for the device for one or more of the programs are dependent on the program states for the device for one or more of the other programs. The server system includes an instruction generation module configured to generate, for the device, a customized instruction that alters operation of the device according to the device-specific set of program states assigned in the altered management plan for the device, where the instruction generation module determines the customized instruction by evaluating, for each of the programs that is active according to the altered management plan for the device, a subset of rules for the program, the subset being associated with a particular program state for the program indicated in the altered management plan. The server system includes a transmission module configured to send, to the device over a communication network, the instruction generated for the device by the instruction module according to the device-specific set of program states assigned in the altered management plan for the device.

In some implementations, the one or more computers are configured to carry out and update device-specific management plans for a plurality of different devices, each of the management plans using different combinations of programs in the predetermined set of programs. The server system is configured to store data indicating the management plans and device-specific program states for each of the plurality of different devices. The program state setting module is configured to alter the management plans for each of the plurality of different devices. The instruction generation module is configured to generate a customized instruction for each of the plurality of devices according to the different sets of device-specific program states for the plurality of devices. The transmission module is configured to send the respective customized instructions to the plurality of devices over the communication network.

In some implementations, the program state setting module is a machine learning model. For example, the program state setting module can include a neural network, a regression model, a decision tree, a support vector machine, a maximum entropy classifier, or other machine learning model.

In some implementations, the server system is configured to communicate individualized application content to the device over the communication network. The server system generates the individualized application content using the plurality of programs and device-specific sets of program states of the programs for the device.

In some implementations, the instruction is configured to cause the device to record a measurement from one or more devices that are in communication with the device through a local wired or wireless data connection.

In some implementations, the server system is configured to: (1) store program status data indicating a set of multiple of the programs that are active for the device a particular time, the program status data also indicating a program state for each of the multiple programs that are active at the particular time, the program state for each program being selected from among the predetermined program states of the program; (2) define a digital state marker as a particular combination of programs being concurrently active with particular program states set for the active programs; (3) identify a group of devices that have previously exhibited the digital state marker by having the particular combination of programs being concurrently active with the particular program states set for the active programs; and (4) determine subsequent program state transitions that were made by the devices in the group after exhibiting the digital state marker.

In some implementations, the server system is configured to: (1) determine that the device exhibits the digital state marker based on the device-specific program states for the device indicating that the particular combination of programs is currently active with the particular program states set for the active programs; (2) automatically vary the device-specific program states of the plurality of programs to assign updated device-specific program states for the device, where the server system assigns the updated device-specific program states for the device in response to determining that the device exhibits the digital state marker and based on the program state transitions made for the devices in the group after the devices in the group exhibited the digital state marker; (3) generate individualized application content for the device by applying, for each of the active programs, the subset of rules associated with the updated program state for the program; and (4) distribute the individualized application content to the device, the individualized application content being generated for the device according to the updated device-specific program states for the device.

In some implementations, the instruction is configured to cause the device to provide an output at the device, where the output includes presentation of text, image, audio, or video by the device or another device in communication with the device.

In some implementations, to alter the management plan for the device, the server system is configured to: automatically enable one or more digital therapeutics programs for a particular user such that the server system initiates use of the enabled program to generate individualized application content, communicate the individualized application content to the device, and instruct the device to present the individualized application content; or automatically disable one or more digital therapeutics programs for the particular user such that the server system discontinues use of the disabled program to generate individualized application content for the particular user.

In some implementations, one or more of the program states of a program correspond to different time periods representing sequential progression through a set of predetermined elements of the program.

In some implementations, one or more of the program states of a program correspond to different levels of intensity or frequency for monitoring, adjusting, or instructing actions of the device, or correspond to different levels of interaction with a user of the device.

In some implementations, the device is a first device, and where the server system is configured to: identify an attribute to be determined for the first device; provide, to a second device, an instruction to acquire information indicative of the attribute of the first device or a user of the first device; and provide, to the first device, one or more instructions to adjust operation of the first device based on information indicative of the attribute of the first device or user of the first device that was received from the second device in response to the instruction to the second device.

In some implementations, the server system is configured to: obtain sensor data from the device; and vary one or more program states of the management plan for the device automatically based at least in part on the sensor data generated by the device.

In some implementations, the server system is configured to: vary the program states of a management plan for the device, the device being associated with a user, where the program states are varied by the server system according to data from (i) at least one general data source providing one or more of weather data, points of interest data, or environmental data, and (ii) at least one user-specific data source from the group consisting of data from a wireless wearable device of the user, data from a medical device of the user, electronic health records for the user, prescription data for the user, genetic data for the user, social media data for the user, and mobile device data from a mobile device associated with the user.

In some implementations, the server system is configured to automatically vary the program states each of a plurality of different devices based on behavioral patterns of respective users of the plurality of different devices to instruct the plurality of different devices to initiate digital therapeutics interventions for the respective users of the plurality of different devices.

In some implementations, the server system is configured to provide data for an administrator interface indicating the device-specific program states for each of one or more of the different devices; where the administrator interface includes controls enabling the administrator to change program states that were automatically assigned by the server system.

In some implementations, the server system is configured to filter rules of the programs to determine the subsets to evaluate. The rules can be pre-associated with different programs and program states, and the server system can filter the rules to select a subset of rules for each program, in which each of the rules in the subset for a program is associated with the program state indicated for the program by the management plan for the device.

In some implementations, the server system is configured to transmit the generated instruction such that the instruction causes the device to carry out one or more actions that alter operation of the device.

In another general aspect, a method includes: storing, by a server system, data indicating a management plan for a device, the management plan indicating a device-specific set of program states for programs in a predetermined plurality of programs, each of the programs having multiple predetermined program states specifying different levels of interaction or different levels of intensity of the corresponding program; altering, by the server system, the management plan for the device by assigning, in the altered management plan, an altered device-specific set of program states corresponding to the plurality of programs, where the server system enforces interdependence of the programs such that the program states for the device for one or more of the programs are dependent on the program states for the device for one or more of the other programs; generating, by the server system, an instruction that alters operation of the device according to the device-specific set of program states assigned in the altered management plan for the device, where the instruction is determined by evaluating, for each of the programs that is active according to the altered management plan, a proper subset of rules for the program, the subset being associated with a particular program state for the program indicated in the altered management plan; and transmitting, by the server system and to the device over a communication network, the generated instruction for the device determined according to the device-specific set of program states assigned in the altered management plan for the device.

In some implementations, a method includes: accessing a database of pharmaceutical data indicating cancer medications and effects of the cancer medications; storing records indicating cancer medications currently or previously used by the first user and current physiological data for the first user; evaluating applicability of the digital therapeutics programs for the first user based on the records for the first user, comprising: (i) determining current or expected effects of cancer medications currently or previously used by the first user; and (ii) determining scores indicating relationships between the determined effects and the digital therapeutics programs. Automatically varying the program states comprises varying the program states for the first user based on the scores indicating relationships between the determined effects for the first user and the digital therapeutics programs.

Other embodiments of these aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 3B, 3C, 3D, and 3E illustrate examples of user interfaces.

Like reference numbers and designations in the various drawings indicate like elements.

DETAILED DESCRIPTION

Figure 1:
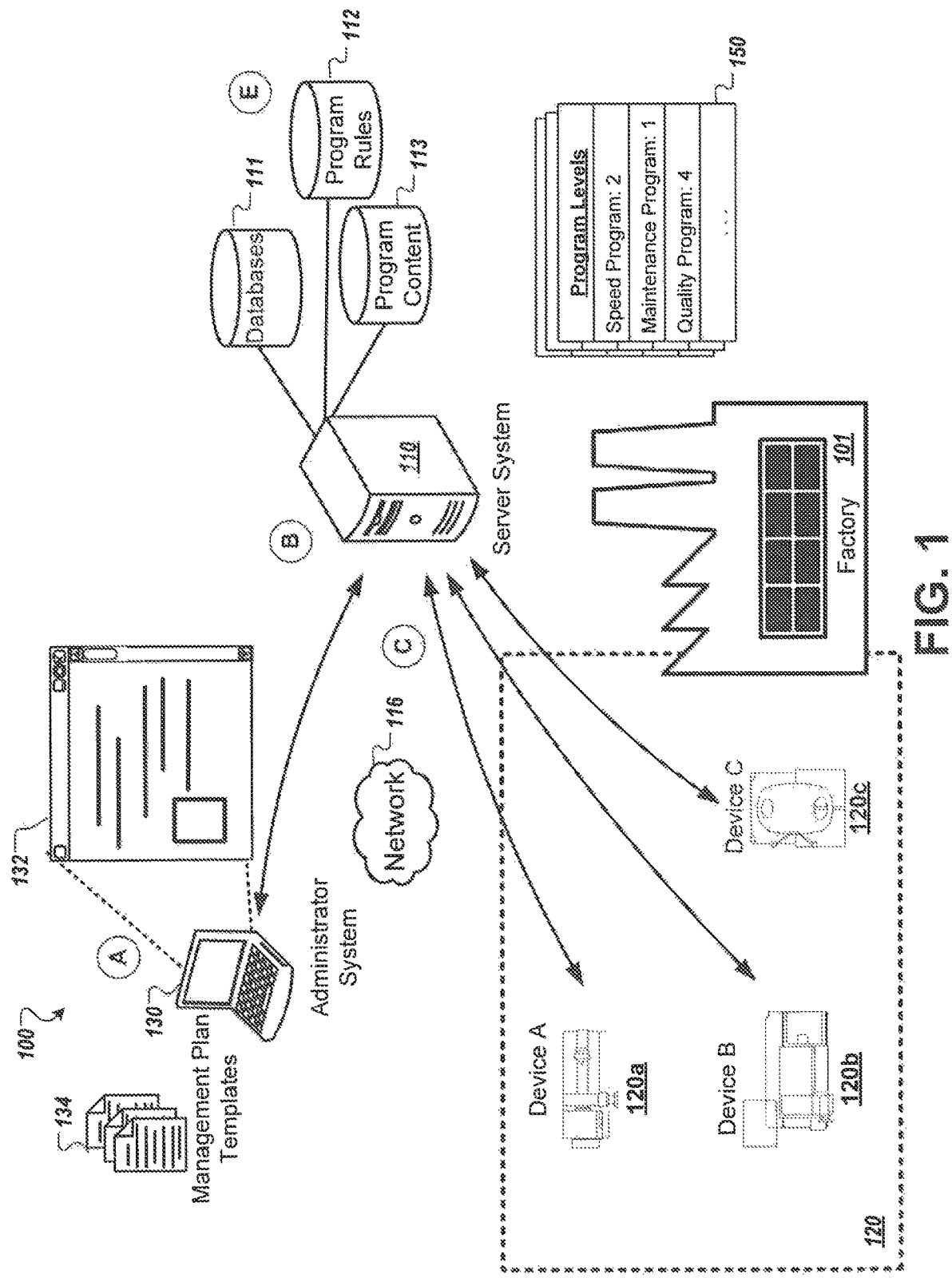
FIG. 1 is a diagram that illustrates an example system for managing devices.

FIG. 1 is a diagram that illustrates an example of a system for managing devices of a factory 101 that includes multiple different devices 120a, 120b, and 120c (collectively, 120). Each of devices 120a, 120b, and 120c is different, and has different characteristics and different operating parameters. The devices 120 can be, for example, devices in factor 101. Factory 101 can includes devices of the same type, e.g., some devices can be the same models and from the same manufacturer; while the devices are of the same model and from the same manufacturer, each of the devices can be unique, and can have unique characteristics that affect the operation and efficiency of each device. For example, a device may be 4 years old, and may have a timing belt of a different thickness from other devices of its make and model. In another example, a different device of the same make and model may be 2 weeks old, and its components may require a break-in period. Thus, while devices can have the same general capabilities or roles, the devices can have different optimal operating conditions and create products of different qualities at different rates.

The system 100 generates dynamic, customized operating plans or management plans for each of the devices. The system 100 includes a server system 110 and an administrator system 130. The server system 110 communicates with each of the other components of the system over a network 116. The server system 110 also accesses a number of data collections, illustrated as databases 111, program rules 112, and program content 113.

The example in FIG. 1 shows various interactions that can be used to create, adjust, and carry out management plans. As described above, the system 100 can generate management plans for a variety of devices. Each device may be associated with one or more users. The characteristics or behavior of the user can be taken into account in determining the programs and levels that are active for a given device. Thus, a management plan may guide or assist in managing actions of the user of the device as well, not only the direct operation of the device, through the outputs and interactions of the device as the management plan is applied.

As an example, interactions shown in stages (A) to (E) follow a process of creating management plans for devices, monitoring each device's status and needs, providing instructions and commands, and adjusting the management plans for each device. The management plan provided by the system is not merely a statement of desired device performance or operating plans. Rather, the management plan provided by the system 100 is a real-time, interactive customized service that initiates communication and interaction with the device or user to carry out operating plans that adjust how devices operate. Among other effects, the management plans can involve interactions, initiated by the system 110 or by a user, that change the device's performance or operation in one or more aspects. The system 100 can operate in an "always-on" manner, frequently or continually assessing a data stream indicating the current status and context of a device (and thus the device's user also), and providing targeted interactions that are relevant to the current and/or estimated future needs of the device and the corresponding user.

During stage (A), the server system 110 generates and provides an administrator portal 132, which may be provided as a web page, web application, data for a locally executable application of the administrator system 130, or in another form. This interactive portal 132 enables the administrator to view management plan templates 134 and select a template to use to enroll a new device, such as a machine or piece of equipment. The portal 132 also provides controls for the administrator to modify the templates 134 for individual devices, as well as view and alter management plans that are currently active for any of the devices assisted by the administrator.

The administrator portal 132 provides a number of management plan templates 134 that the administrator can select when enrolling a new device. In some instances, the templates correspond to different areas or fields that a user wishes to manage. The management plans can be generated as combinations of different digital operating programs. A template 134 can specify a set of these programs that are made inactive for a given device. The programs each have a number of components and states that very how they interact with the device. For example, each program may include multiple segments that are applicable over different time periods. The program can define a sequence of these segments, or multiple different sequences. The segments may correspond to fixed length periods, for example, a week, or month, or another fixed or standardized time period. Alternatively, one or more of the periods may have a variable duration.

Each program has various levels or intensities with which the program applies. Different levels may correspond to different levels of need. In some implementations, different levels of a program, may respond to different objectives or conditions.

When a device is first enrolled, the management plan template 134 selected by the administrator specify a default set of programs and corresponding levels for the device. The administrator may manually adjust the selections, for example, by adding or removing programs, and increasing or decreasing the levels of programs. In this matter, the administrator can specify an initial management plan that meets the needs identified by the device.

With the interfaces and tools provided by the server system 110 through the administrator portal 132, an administrator can efficiently manage management plans for a large number of devices. In many instances, after the management plan is initiated, the administrator does not need to further modify or adjust the management plan. The server system 110 automatically adjusts each individual management plan according to the unique set of user input and sensor data detected for each device. Nevertheless, an administrator can view an individual device's progress and, if appropriate, adjust a device's management plan manually through the administrator interface 132. As the server system 110 adjusts the management plans based on each device's individual circumstances, different management plans will have different segments of programs, different levels of the programs, and different combinations of the programs active. These differences as well as the application of individual program rules to unique device data sets, provide a unique experience to each user.

During stage (A), the server system 110 stores information about each device enrolled in the system. The server system 110 can store the information using a data storage subsystem which may include, for example, direct attached storage (e.g., hard drives, solid state drives, etc.), locally attached storage, network attached storage (NAS), one or more databases, a storage area network (SAN), a database management system (DBMS) and/or one or more database servers, or other elements. For example, the data storage subsystem may include one or more relational databases (e.g., an SQL database), one or more object-oriented databases, one or more noSQL databases (e.g., a key-value database, a wide column store database, etc.), a distributed data store, one or more file systems, or other data storage system. This data storage subsystem can store data gathered from devices being managed (e.g., state information, sensor data, operation history, etc.) as well as information that the server system 110 generates (e.g., current and prior levels for different programs, instructions to devices, source content and generated content to be transmitted to devices, etc.). As discussed further below, the server system 110 stores data indicating the current state of a device's management plan, such as the programs that are active, the levels of each program, which segment the user is currently in for each program, and so on. In addition, the server system 110 stores historical information about the device and its/his interactions with the application and progress while using the management plan. The server system 110 can acquire data from many different sources including surveys, sensor data, and other data discussed further below. This information can be stored in various databases 111.

The operating characteristics of a device can be determined and used to adjust the operation of a device to optimize for different goals. A device's operation can be adjusted for improved efficiency, maximum accuracy, increased speed, etc. By performing actions to adjust the operating characteristics different goals can be achieved. These actions can be determined based on the operating characteristics, and can be governed by a plan for each device 102. The action can be selected based on factors including underlying causes for the device's operating characteristics. Each action can affect or account for operating conditions of the devices. For example, if a device has low accuracy due to operating at a high spindle speed, actions can include slowing down the production rate of the device (e.g., so the spindle speed decreases and accuracy increases), adding quality control checks to the device's outputs, etc. The operation of other devices may also be adjusted in response, for example, so that a second device implements more frequent or detailed quality checks for the first device, or so that another device increases production rate to compensate for the decreased production of the first device.

As another example, if a device consistently needs to be shut down for a cooling-down period, slowing down the production rate of the device can decrease the frequency with which the device needs to cool-down. For example, a high work pace can induce high heat levels at various points and components of the device. A reduction in pace affects various operating characteristics of the device, such as tendency to overheat, work piece tolerances, etc.

The actions can depend on underlying and/or interrelated characteristics of the device. A change in the spindle speed of the device can produce effects in addition to an intended or expected effect. For example, if a device's work pace is faster than other devices, the rushed production cycle can reduce the accuracy of a device's work, and the fast pace can increase the heat levels at the device at various moving parts, thus increasing the frequency with which the device must be cooled down. In another example, flagging the device's work for review decreases the speed at which the device can turn out products, and increases accuracy while decreasing the chances of overheating the device. With fewer overheating incidents, the frequency of unexpected repairs to the device can decrease.

During stage (B), the server system 110 also stores information that defines each of the programs. Each program can include a corresponding set of program rules 112. A repository of these rules 112 is maintained and accessed by the server system 110, and the rules are evaluated on an ongoing basis to determine when to communicate with each device and in what manner. If a device has multiple programs active, rules for each program separately can specify different communications to be provided to the device.

In some applications, devices can have common stages within their operational lifetime, or can have common operating conditions for which a general set of actions can account. For example, if devices nearing the end of their useful life commonly have lower accuracy and lower efficiency, and these degradations in work product quality can be addressed using a common set of actions across different devices or different types of devices, the common set of actions can be collected and applied to each device at the end stage of its operational lifetime. This common set of actions can be standardized as a program, and can be generated based on data collected from multiple devices over time. These programs can be tailored to different aspects of the devices. For example, a program for older devices can include preventative measures to decrease the chances of unexpected failures by scheduling more frequent quality assessments, lower production targets and speeds, flagging the device for review, etc. If older devices are scheduled for more frequent maintenance checks, any potential problems can be diagnosed and repaired as soon as they present.

The rules for the programs have conditions and triggers associated with them. Each rule may have a condition that must be satisfied for a corresponding system action of the rule to be performed. In addition, a rule can have a trigger or triggering condition associated with it, so that the action of the rule occurs when the trigger is satisfied as well as one or more other associated conditions.

The actions of the server system 110 to generate user specific interfaces and content can draw from a repository of program content 113. This repository 113 can include media, messages, and other content that is selectively provided according to the program rules in the repository 112, which in turn are selectively used according to which programs are active, which levels of the programs are active, and which segments of the programs are active.

The server system 110 provides a set of program data 150 that indicates the active programs and levels of each active program for each of the devices 120a, 120b, and 120c.

During stage (C), the server system 110 obtains data for each of the various users enrolled with the management plan. The server system 110 communicates with devices 120 to acquire data for each of the various devices in rolled with the management plan. The server system 110 communicates with devices 120 to acquire context information, such as the location of the respective device, a current activity of the device, sensor data, and other data. The server system 110 also communicates with third-party systems to access data such as device activity and interactions, and even general information such as current news, weather, and other data.

In stage (D), the server system 110 applies the individual management plan for each device to the data collected for the device. For example, the rules that are applicable to an active segment of an active program are evaluated using the context information historical information and other data. Although different programs may indicate different messages to be provided or different instructions to present to a device, the server system 110 may integrate the content across the various programs.

During stage (E), the server system 110 adjusts the states of the programs if appropriate. The server system 110 can assess various factors to determine whether the set of programs that is active should change, and whether the levels and active segments of each program should change. In some instances, a device progresses through segments of a program based on the passage of time. The server system 110 can detect when an appropriate transition from one time. To the next occurs, and so when the change in applicable rules occurs.

The server system 110 can include a program state setting module to evaluate and change the states of programs in each management plan. Using the program state setting module, the server system 110 can assess various factors to determine whether the set of programs that is active should change, and whether the levels and active segments of each program should change. In some instances, a device or user progresses through segments of a program based on the passage of time. The program state setting module of the server system 110 can detect when an appropriate transition should occur from one time period or one section of a program to another. In general, the program state setting module can include software and/or hardware that accesses data indicating current program states for a device or user, evaluates data received from the device or user or from other sources, and sets program states for the management plan of the device or user as a result of the evaluation. The program state setting module may perform these operations iteratively, e.g., periodically, for example every. As another example, the program state setting module may re-evaluate the program states for a device or user in response to receiving additional information, such as sensor data, user input, data characterizing the operation of a device, or other input. As discussed below, the program state setting module may set the program state for one or more of the programs based on the program states of one or more other programs, so that the program states are interdependent.

The server system 110 can include an instruction generation module that generates customized instructions to alter the operation of the managed devices according to the updated program states for each device. The instruction generation module can include one or more software modules that access device-specific or user-specific program states for a device, determine appropriate rules from the programs that correspond to the states, apply the determined rules (e.g., evaluate a subset of the rules for a program to determine which rules have conditions and triggers satisfied), and generate instructions for the device to carry out system actions indicated by the rules. The rules that are applicable to an active segment of an active program can be evaluated using the context information historical information and other data. The instructions generated may cause any of a variety of changes in the operation of a device, including, but not limited to, initiating and reporting a measurement with a sensor of the device or a connected device, opening or closing an application, increasing or decreasing a frequency of sensor measurements made or outputs made by a device, switching an operating mode (e.g., entering or exiting a low-power mode), altering the appearance of a user interface, presenting certain information or media by the device (e.g., audibly, visually, or haptically), altering the set of interactive controls made presented on the device, altering threshold or triggers that the device applies, initiating a communication session between the device and another device.

The instruction generation module can operate using any of a variety of techniques. For example, the instruction generation module may determine appropriate program levels, identify content (e.g., media, templates, sets of potential instructions, etc.) corresponding to those levels, and then generate customized instructions as a selection from the identified content. The instruction generation module may filter or narrow the content for specific program levels based on the prior history for a device or user (e.g., based on effectiveness of prior instructions, based on current and prior context information for the device or user, to avoid repeating instructions given recently, and so on.) As another example, the instruction generation module may access a machine learning model for generating instructions, provide an indication of the program states for a device or user to the machine learning model, and receive output indicating types of content or instructions likely applicable based on the program states. The instruction generation module may use the output of the machine learning model to retrieve or generate data elements that are sent in the customized instructions. As another example, the instruction generation module may access one or more templates for instructions and populate the templates with elements selected based on the device-specific or user-specific program states for a device and based on the current and historical information about a device or its user.

The server system 110 can include a transmission module to send customized instructions to devices. For example, the transmission module may include a network interface controller, such as a LAN adapter, WAN adapter, network interface card, or other electronic circuitry (potentially with associated firmware and/or software) configured to communicate using a physical layer and data link layer standard such as Ethernet or Wi-Fi. As customized instructions are determined for the various devices, the server system 110 sends instructions causing the devices to vary their operation and outputs using the transmission module, over a network, such as the Internet, a local area network, a wide area network, etc.

Figure 2:
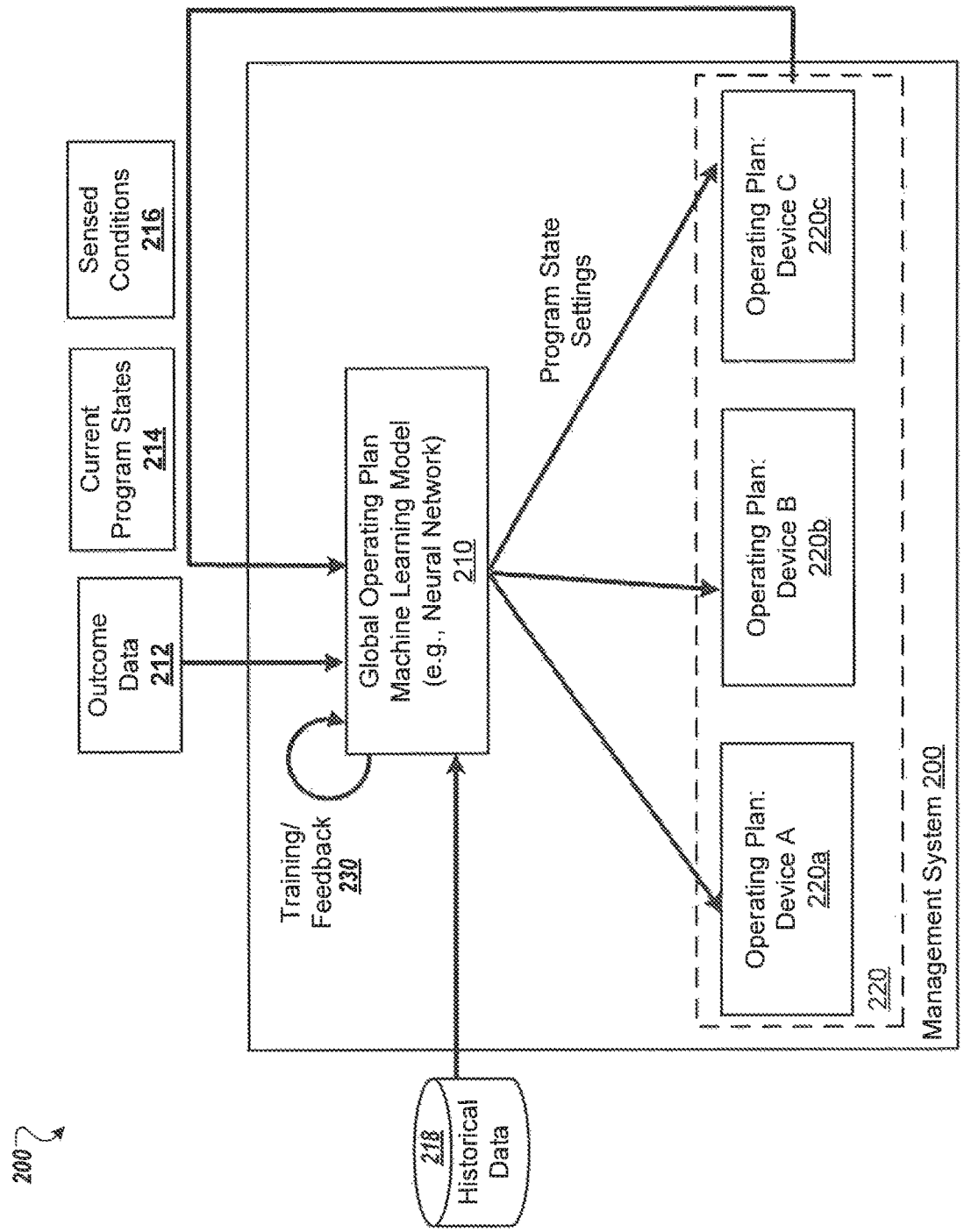
FIG. 2 is a diagram that illustrates an example learning and training system for managing devices.

FIG. 2 shows an example management system 200. The management system 200 is an example of a system implemented as computer programs on one or more computers in one or more locations (e.g., one or more server systems) in which the systems, components, and techniques described below are implemented.

The management system 200 selects operating plans, or a progression of programs, to be applied in order to manage devices within complex system 100 determined based on training/feedback data 230. That is, the management system 200 receives training/feedback data 230, such as current program states 214 of the devices of complex system 100, sensed conditions 216 of the devices of complex system 100, and/or outcome data 212 of the devices of complex system 100. In response to the training/feedback data 230, the management system 200 generates a global operating plan output using the global operating plan neural network 210. In some examples, each observation includes raw sensor data captured by one or more sensors, such as visual data, inertial measurement unit (IMU) readings, and so on. The training/feedback data 230 can be specific to a particular device 120a, 120b, and 120c of the complex system 100. In some examples, the training/feedback data 230 is applicable across the complex system 100 generally, allowing the machine learning model(s) of the system 200 to discover and re-create response patterns that transition from one desired set of programs and levels to another more desirable set of programs and levels.

The global operating plan neural network 210 is a neural network that is configured to receive an observation in the form of input data, such as training/feedback data 230 and to process the observation to generate a global operating plan output in accordance with current values of the parameters of the global operating plan neural network 210. The global operating plan output defines a probability distribution over a set of possible actions to be performed in order to manage devices within the complex system 100, e.g., device 120a, 120b, and 120c. For example, the global operating plan output may include a mean action vector and covariances of the entries of the mean action vector. In this example, the global operating plan output includes a mean action vector that includes a respective entry, i.e., a respective mean spindle speed, for each device tool and covariances of the entries of the mean action vector.

To effectively tailor respective operating plans for particular devices in response to training/feedback data 230, the management system 200 trains the global operating plan neural network 210 to determine trained values of the parameters of the global operating plan neural network 210. The global operating plan neural network generates an operating plan 220a, 220b, and 220c for each of the respective devices 120a, 120b, and 120c. Each of the operating plans includes a progression of program state settings for the particular device.

Generally, the management system 200 performs multiple iterations of a two-step training approach to train the global operating plan neural network 210.

Instead of directly learning the parameters of the global operating plan neural network 210, in the first step of the training approach the management system 200 uses a progressive, or trajectory-centric, algorithm to learn simple operating plans for a particular device (e.g., device 102a, 102b, or 102c) of the complex system 100. The global operating plan neural network 210 is trained based on feedback 230 from the operating plans 220a, 220b, and 220c. Feedback 230 includes data such as outcome data 212, current program states 214, sensed conditions 216, and historical data 218.

Outcome data 212 includes data indicating the outcomes of the application of the operating plans to respective devices. For example, whether a particular operating plan effected an improvement can be recorded as outcome data 212. Outcome data 212 can be generated or collected by the global operating plan neural network 210. In some example, outcome data 212 can be received from the operating plans 220 or the devices 120.

Current program states 214 include data that indicates the status of each program as applied to each of the respective devices at the time feedback 230 is collected. Current program states 214 can also include feature vectors that represent a respective device. For example, a feature vector for a particular device can indicate that it is 8 years old, and has poor battery life. Sensed conditions 216 include data collected by, for example, sensors (e.g., temperature sensors, digital scales, optical sensors, cameras, inductive sensors, motion sensors, microphones, ultrasonic sensors, etc.). Sensed conditions 216 can include external conditions, such as the temperature, an air quality index, a speed, a direction, etc. or internal condition of a device. Current program states 214 and sensed conditions 216 can be received from the operating plans 220 or the devices 120.

Historical data 218 includes historical values for various feedback, including historical values for outcome data 212, current program states 214, and sensed conditions 216. Historical data 218 can be collected and stored in a storage medium by the global operating plan neural network 210. In some examples, historical data 218 can be stored in a storage medium by the operating plans 220 or devices 120.

In particular, for each one of these devices 120a, 120b, and 120c, the management system 200 generates an operating plan by selecting programs to be applied in order to manage the devices 120. The feature vector includes the various programs and levels for which In particular, for each device, the management system 200 determines the state-to-state transition, or operating plan, using the global operating plan neural network 210 and in accordance with the current operational characteristics of each device. The global operating plan neural network 210 receives, for example, a feature vector representing a particular device. The system can generate an operating plan in accordance with current values of the parameters of the global operating plan neural network 210. That is, the system can receive a sequence of observations, or input data (e.g., training/feedback data 230) and, in response to each observation in the sequence, process the observation using the global operating plan neural network to generate a global operating plan output for the observation in accordance with current values of the parameters and then sample an action from the distribution defined by the global operating plan output.

The management system 200 then optimizes a respective operating plan 220a, 220b, or 220c for each device 120a, 120b, or 120c. That is, for each device, the management system 200 optimizes an operating plan that is specific to the device on the progression of programs and program levels for the device.

In the second step of the training approach, after optimizing the operating plans 220a, 220b, and 220c, the management system 200 uses the optimized operating plans to create a training set for learning a complex high-dimensional global plan in a supervised manner. That is, the management system 200 generates training data for the global operating plan neural network 210 using the optimized operating plans 220 and trains the global operating plan neural network 210 on the training data to adjust the current values of the parameters of the global operating plan neural network 210, e.g., using supervised learning. The management system 200 can train the global operating plan neural network 120 using only received observations (e.g., training/feedback data 230), and, thus, the global operating plan neural network 210 is able to predict actions from the training/feedback data 230.

The management system 200 can effectively use the global operating plan neural network 210 to select programs to be applied in order to manage the devices 120a, 120b, and 120c once the global operating plan neural network 210 has been trained. In particular, when an observation is received, the management system 200 can process the observation using the global operating plan neural network 210 to generate a global operating plan output in accordance with the trained values of the parameters of the global operating plan neural network 210. The management system 200 can then select a new program or program level to apply to manage the devices 120a, 120b, and 120c in response to new training/feedback data 230. For example, if training/feedback data 230, specific to device 120c, is received, the global operating plan neural network 210 can process the training/feedback data 230 and learn globally across the complex system 100, as well as apply an action trajectory specific to device 120c.

In some implementations, the global operating plan neural network 210 includes a convolutional sub-network (e.g., as an initial processing portion of the network) and a fully-connected sub-network.

The management system 200 can train the global operating plan neural network 210 on the training data to adjust the current values of the parameters of the global operating plan neural network 210 by, in some examples, adjusting current values of the fully-connected parameters while holding current values of the convolutional parameters fixed. In some other examples, the system 200 can train the global operating plan neural network 210 on the training data to adjust the current values of the parameters of the global operating plan neural network 210 by adjusting current values of the fully-connected parameters and current values of the convolutional parameters.

In some implementations, the system 200 pre-trains the convolutional sub-neural network with a proxy pose detection objective to determine pre-trained values of the convolutional parameters, i.e., prior to training the neural network 210 using the two-step approach.

Additionally, in some implementations, in addition to or instead of pre-training the convolutional sub-neural network, the system 200 pre-trains the neural network 210 on training data generated as a result of conventional global policy search with operating plan optimization performed for each device 120a, 120b, and 120c.

The system can repeatedly perform the training process until termination criteria for the training of the global operating plan neural network are satisfied to determine trained values of the parameters of the global operating plan neural network. For example, the system can perform the training process for a particular amount of time, until a certain number of iterations of the training process have been performed, or until the global operating plan neural network 210 achieves a threshold level of performance across the operating plans 220.

Figure 3A:
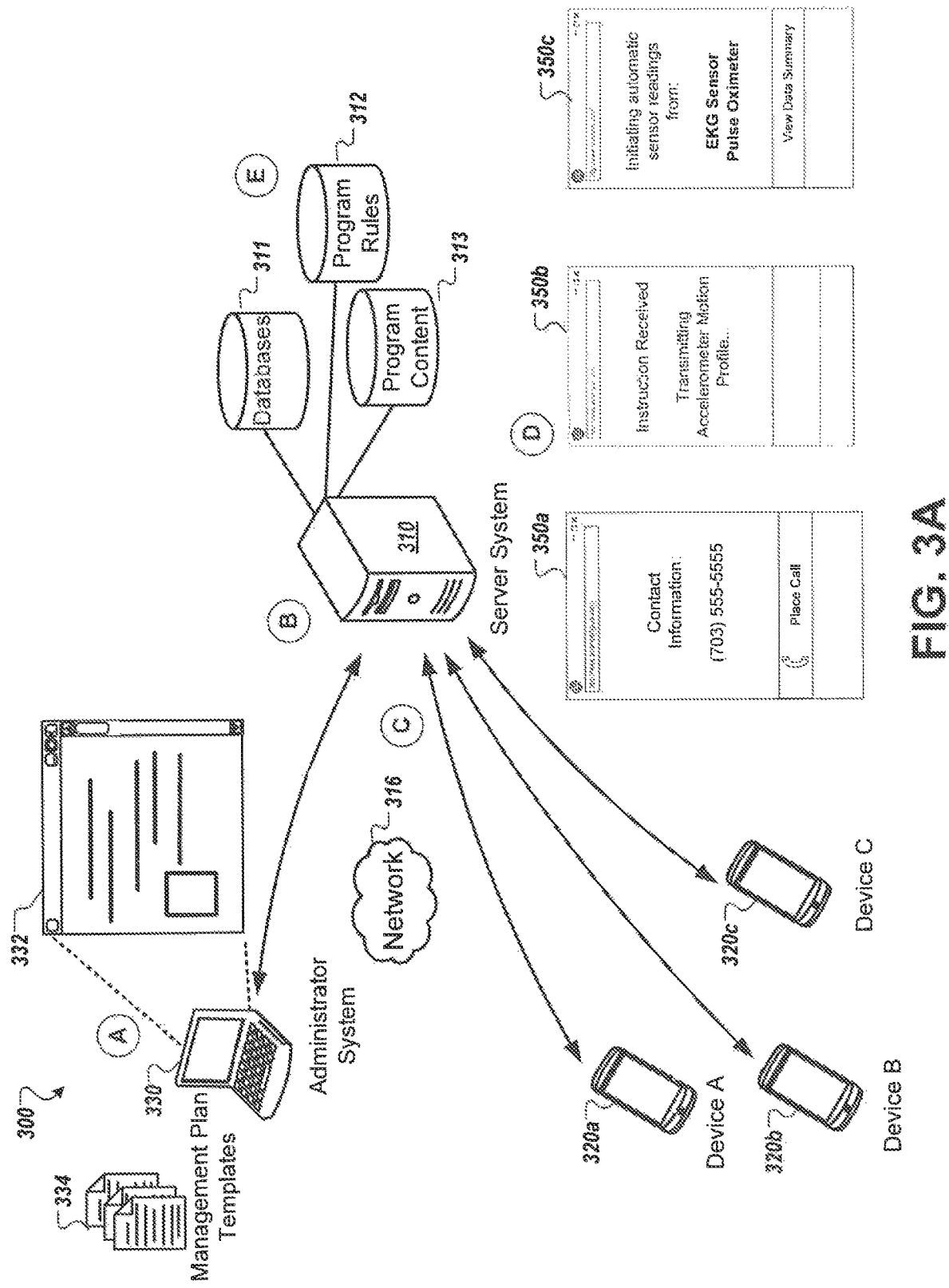
FIG. 3A is a diagram that illustrates an example of a generalized system for generating dynamic, customized management plans for each of the devices.

FIG. 3A is a diagram that illustrates an example of a generalized system 300 of network connected devices for generating dynamic, customized management plans for each of the devices. The system 300 includes a server system 310, client devices 320a, 320b, and 320c, an administrator system 330, and additional systems 440a, 440b, and 440c. The server system 310 communicates with each of the other components of the system over a network 316. The server system 310 also accesses a number of data collections, illustrated as databases 311, program rules 312, and program content 313.

The example in FIG. 3A shows various interactions that can be used to create, adjust, and carry out management plans. As described above, the system 300 can generate management plans for a variety of complex systems. The situation in which a user is the complex system for whom the management plan is generated is described solely for ease of illustration. As an example, interactions shown in stages (A) to (E) follow a process of creating a management plan, monitoring the device's status and needs, providing instructions of commands, and adjusting the management plan for each device. The management plan maintained and administered by the system is not merely a statement of desired device performance or operating plans. Rather, the management plan provided by the system 300 is a real-time, interactive customized service that initiates communication and interaction with the managed device and/or the device's user to adjust operation of the device. Among other effects, the management plan can generate instructions, initiated or triggered by the system 310 in response to sensor data or other detected events, that change the device's performance or mode of operation, including various outputs of the device.

During stage (A), the server system 310 generates and provides an administrator portal 332, which may be provided as a web page, web application, data for a locally executable application of the administrator system 330, or in another form. This interactive portal 332 enables the administrator to view management plan templates 334 and select a template to use to enroll a new device or user. The portal 332 also provides controls for the administrator to modify the templates 334 for individual users, as well as view and alter management plans that are currently active for any of the users assisted by the administrator. Examples of other information that can be provided include indications of performance targets (e.g., goals) and progress over time as shown in FIG. 3E.

The administrator portal 332 provides a number of management plan templates 334 that the administrator can select when enrolling a new device or user. In some instances, the templates correspond to different areas or fields that a user wishes to manage. The management plans can be generated as combinations of different digital operating programs. A template 334 can specify a set of these programs that are made inactive for a given device or user. The programs each have a number of components and states that very how they interact with the device or user. For example, each program may include multiple segments that are applicable over different time periods. The program can define a sequence of these segments, or multiple different sequences. The segments may correspond to fixed length periods, for example, a week, or month, or another fixed or standardized time period. Alternatively, one or more of the periods may have a variable duration.

Each program has various levels or intensities with which the program applies. The level of the program may affect, for example, how frequently the program communicates with the device or instructs the device to present output to a user, how ambitious or difficult the goals and activities of the program are, how closely behavior is monitored, and so on.

When a device or user is first enrolled, the management plan template 334 selected by the administrator specify a default set of programs and corresponding levels for the user. The administrator may manually adjust the selections, for example, by adding or removing programs, and increasing or decreasing the levels of programs. In this matter, the administrator can specify an initial management plan that meets the needs identified by the device, user, or other users, such as the user's support system.

With the interfaces and tools provided by the server system 310 through the administrator portal 332, an administrator can efficiently manage management plans for a large number of user. In many instances, after the management plan is initiated, the administrator does not need to further modify or adjust the management plan. The server system 310 automatically adjusts each individual management plan according to the unique set of user inputs, sensor data, and behavior detected for each device or user. Nevertheless, an administrator can view an individual device or user's progress and, if appropriate, adjust a device or user's management plan manually through the administrator interface 332. As the server system 310 adjusts the management plans based on each device or user's individual circumstances, different management plans will have different segments of programs, different levels of the programs, and different combinations of the programs active. These differences as well as the application of individual program rules to unique device or user data sets, provide a customized progression of operating states to each device and a unique experience to each user.

During stage (A), the server system 310 stores information about each device or user enrolled in the system. As discussed further below, the server system 310 stores data indicating the current state of a device or user's management plan, such as the programs that are active, the levels of each program, which segment the user is currently in for each program, and so on. In addition, the server system 310 stores historical information about the device or user and its/his interactions with the application and progress while using the management plan. The server system 310 can acquire data from many different sources including surveys, sensor data, and other data discussed further below. This information can be stored in various databases 311, which are shown as one example of a data storage subsystem.

The server system 310 can store the data using a data storage subsystem which may include, for example, direct attached storage (e.g., hard disk drives, solid state drives, etc.), locally attached storage, network attached storage (NAS), one or more databases, a storage area network (SAN), a database management system (DBMS) and/or one or more database servers, or other elements. For example, the data storage subsystem may include one or more relational databases (e.g., an SQL database), one or more object-oriented databases, one or more noSQL databases (e.g., a key-value database, a wide column store database, etc.), a distributed data store, one or more file systems, or other data storage system. This data storage subsystem can store data gathered from devices being managed (e.g., state information, sensor data, operation history, etc.) as well as information that the server system 310 generates (e.g., current and prior levels for different programs, instructions to devices, source content and generated content to be transmitted to devices, etc.).

During stage (B), the server system 310 also stores information that defines each of the programs. Each program can include a corresponding set of program rules 312. A repository of these rules 312 is maintained and accessed by the server system 310, and the rules are evaluated on an ongoing basis to determine when to communicate with each device or user and in what manner. If a plan has multiple programs active, rules for each program separately can specify different communications or interventions to be provided to the user. Some examples include altering operation of a device, initiating a scan of an environment nearby, acquiring data indicating a state of a device, discovering and issuing commands to nearby devices, providing media to a user (e.g., text, audio, video, etc.) using the output devices of a device (e.g., display screen, speaker, vibrator, etc.), generating an interactive form such as a survey for the user, sending a notification email or other message, challenging, reminding, or informing the user about a goal, providing recommendations, providing content from a social media platform, providing instructional activities or games, and so on. These and other interactions can also be provided to friends, family members, medical service providers, and others to support the user. For example, surveys or recommendations can be generated and sent to friends and family of a user, to corroborate conditions indicated by the detected behavior or interactions of the user. In this manner, the various programs can support a user in some way, through interactions with one or more other associated users of the system. In some instances, these types of interactions may provide better results than changing the operation of the user's device.

The rules for the programs have conditions and triggers associated with them. Each rule may have a condition that must be satisfied for a corresponding system action of the rule to be performed. In addition, a rule can have a trigger or triggering condition associated with it, so that the action of the rule occurs when the trigger is satisfied as well as one or more other associated conditions.

The actions of the server system 310 to generate device-specific or user-specific interfaces and content can draw from a repository of program content 313. This repository 313 can include media, messages, and other content that is selectively provided according to the program rules in the repository 312, which in turn are selectively used according to which programs are active, which levels of the programs are active, and which segments of the programs are active.

During stage (C), the server system 310 obtains data for each of the various users enrolled with the management plan. The server system 310 communicates with devices 320a, 320b, and 320c to acquire data for each of the various users in rolled with the management plan. The server system 310 communicates with devices 320a, 320b, and 320c to acquire context information, such as the location of the device, a current activity of the device, sensor data, and other data. Each of the devices 320a, 320b, and 320c can have a respective user for whom the management plans apply. The server system 310 also communicates with third-party systems to access data such as user activity and interactions, and even general information such as current news, weather, and other data.

In stage (D), the server system 310 applies the individual management plan for each device or user to the data collected for the device or user. For example, the server system can include an instruction generation module that generates customized instructions to alter the operation of the managed devices according to the updated program states for each device. The instruction generation module can include one or more software modules that access device-specific or user-specific program states for a device, determine appropriate rules from the programs that correspond to the states, apply the determined rules (e.g., evaluate a subset of the rules for a program to determine which rules have conditions and triggers satisfied), and generate instructions for the device to carry out system actions indicated by the rules. The rules that are applicable to an active segment of an active program are evaluated using the context information historical information and other data. The instructions generated may cause a variety of changes in the operation of a device, including, but not limited to, initiating and reporting a measurement with a sensor of the device or a connected device, opening or closing an application, increasing or decreasing a frequency of sensor measurements made or outputs made by a device, altering an operating mode (e.g., entering or exiting a low-power mode), altering the appearance of a user interface, presenting certain information or media by the device (e.g., audibly, visually, or haptically), altering the set of interactive controls made presented on the device, altering threshold or triggers that the device applies, initiating a communication session between the device and another device.

The instruction generation module can operate using any of a variety of techniques. For example, the instruction generation module may determine appropriate program levels, identify content (e.g., media, templates, sets of potential instructions, etc.) corresponding to those levels, and then generate customized instructions as a selection from the identified content. The instruction generation module may filter or narrow the content for specific program levels based on the prior history for a device or user (e.g., based on effectiveness of prior instructions, based on current and prior context information for the device or user, to avoid repeating instructions given recently, and so on.) As another example, the instruction generation module may access a machine learning model for generating instructions, provide an indication of the program states for a device or user to the machine learning model, and receive output indicating types of content or instructions likely applicable based on the program states. The instruction generation module may use the output of the machine learning model to retrieve or generate data elements that are sent in the customized instructions. As another example, the instruction generation module may access one or more templates for instructions and populate the templates with elements selected based on the device-specific or user-specific program states for a device and based on the current and historical information about a device or its user.

Among other features discussed above, the instruction generation module allows the system 310 to determine, for each particular program and each particular device or user at the current time, what information should be requested through a survey perhaps or what information should be provided to the device or user. The instruction generation can be done for each of the programs that are active in the device or user's management plan, or holistically for the combination of programs as a whole. For example, the server system 310 can take all of the results of the different programs (e.g., changes in operation of the device indicated by those programs) in the management plan and generate customized user interface data to be sent to the appropriate device or device of the user. Although different programs may indicate different messages to be provided or different survey questions to present to a user, the server system 310 may integrate the content across the various programs.

As the user interface data is provided to the devices 320a, 320b, and 320c, users interact with the digital management plan application on their devices 320a, 320b, and 320c. Data indicating inputs to the application and the manner in which the user acts in response to the communication are determined and provided to the server system 310, which logs this information. For example, if a user is shown a message recommending they go outside and take advantage of the good weather, and subsequently does go outside as detected by motion sensors and location sensors of the device, the server can store this information and use it to determine future content for the user. Examples of user interfaces showing user interfaces that may be provided on the user devices 320a, 320b, and 320c are shown in elements 350a, 350b, and 350c, which are shown in an expanded view in FIGS. 3B, 3C, and 3D.

The server system 310 can include a transmission module to send customized instructions to devices. For example, the transmission module may include a network interface controller, such as a LAN adapter, WAN adapter, network interface card, or other electronic circuitry (potentially with associated firmware and/or software) configured to communicate using a physical layer and data link layer standard such as Ethernet or Wi-Fi. As customized instructions are determined for the various devices, the server system 310 sends the instructions to cause the devices to vary their operation, e.g., to change their outputs and/or internal functioning, using the transmission module, over a network, such as the Internet, a local area network, a wide area network, etc.

FIGS. 3B, 3C, and 3D illustrate that the user interface provides different user-selectable controls, such as buttons, links etc., and different content in the user interface of a device. For example, in FIG. 3B, when contact information, such as a telephone number, is shown, an action button to place a call is available. In FIG. 3C, the user interface reflect that the device was instructed to acquire data from sensors of the device, such as an accelerometer. In FIG. 3D, the device was instructed to acquire information from another device, in this case a pulse oximeter and an EKG sensor, and the device performs those actions and provides the results to the server system 310.

During stage (E), the server system 310 adjusts the states of the programs if appropriate. The server system 310 can include a program state setting module to evaluate and change the states of programs in each management plan. Using the program state setting module, the server system 310 can assess various factors to determine whether the set of programs that is active should change, and whether the levels and active segments of each program should change. In some instances, a device or user progresses through segments of a program based on the passage of time. The program state setting module of the server system 310 can detect when an appropriate transition should occur from one time period or one section of a program to another. In general, the program state setting module can include software that accesses data indicating current program states for a device or user, evaluates data received from the device or user, and then sets program states for the device or user to use going forward. The program state setting module may perform these operations iteratively, e.g., periodically, for example every. As another example, the program state setting module may re-evaluate the program states for a device or user in response to receiving additional information, such as sensor data, user input, data characterizing the operation of a device, or other input. As discussed below, the program state setting module may set the program state for one or more of the programs based on the program states of one or more other programs, so that the program states are interdependent.

Transitions between states or levels of programs can be based on measures of performance determined by or entered to a device, which can be assessed with respect to certain targets for goals, which may be standardized or maybe device or user specific. For example, a program for physical activity may set a goal of a number of steps per day for the user to walk. When a user successfully completes ago the system may determine that a level corresponding to a higher goal is appropriate. In some instances, a higher level represents a need for greater intervention or monitoring. As a result, or user who successfully completes goals for physical activity may be transitioned automatically to a lower level of the physical activity program in which fewer reminders or interactions are provided, since the user has shown the ability and willingness to exercise. On the other hand, are user who is not exercising to the extent needed, or who is not responding to the interventions of the program may be transitioned to a higher level indicating more intense or different types of interaction in an attempt to improve the users physical activity.

Thus, by varying the level of each program as management proceeds through different program segments, the server system 310 can tailor the degree of interaction and intensity of support across various aspects of the user's wellbeing and lifestyle.

When adjusting the programs in a management plan, the levels or states of the programs can be interdependent. Changes in the level of one program may result in changes to other programs. These interdependent level transitions may depend on more than simply the levels of other programs, and maybe based on any of the data collected from or about a user as well, as well as any of the outputs of the different programs.

One of the ways that the server system 310 interacts with users is to provide interactive forms and surveys. Each form can be customized or dynamically created for a user's current status and the current state of his management plan. These forms can request information that is indicative of the user's progress with respect to one or more active programs in the management plan. Similarly, the surveys may include questions or other interactive activities that would enable the server system 310 to evaluate whether additional programs should be activated. The server system 310 may use a variety of computer adaptive testing techniques to generate forms that acquire sufficient information needed to determine her use of progress for various programs, without overburdening the user.

As an example, each of the programs that are active in a management plan may indicate, periodically or intermittently, types of data needed from a device or user. Even for a single program, the type of data needed may vary over time. For example, different segments of a program may correspond to different combinations of topics. Different levels may require different frequencies of input or different precision of input. Thus, each program may provide a list of data items to obtain from a user. The server system 310 and may assess these lists to generate appropriate interactions that obtain the appropriate information and benefits the user.

The server system 310 may de-duplicate the set of data items so that multiple redundant questions are not asked. The server system 310 also checks recent answers and interactions of the device or user, as well as any other data sources (e.g., location data, sensor data, online activity, communications of family and friends with the server system, etc.) to determine if the requested information is available from other sources already. For the remaining items that are not yet available, the server system 310 may prioritize or schedule the data acquisition to reduce the overall burden of any one interaction and increase the likelihood that the user will complete the form successfully.

The server system 310 may group the remaining data items into related groups. For example, the data needed by multiple programs may be acquired through a single form, and in some instances multiple items of data may be able to be obtained through a single question.

The server system 310 can access a database of questions and interactive activities, with each item having metadata specifying the types of data obtained through the question or activities. Thus, by mapping needed data types to the various types of interactions in the database, the server system 310 selects a few questions or interactions that can acquire the needed input.

The server system 310 may implement the survey or form generation process to allow significant flexibility. Individual programs may provide fully formed questions or interactive elements to be incorporated into a user interface. In addition, or as an alternative, programs may simply provide an indication of data types to be acquired, and the system 310 can formulate appropriate questions and user interface elements for obtaining the data. As noted above, the server system also may combine and integrate the requests needed by various programs.

In many cases, the questions and interactions in a survey are adapted to normal daily life of the user. For example, valuable information can be obtained through journal entries a user enters in association with the application. The application can ask about the user's plans, recommend a friend to reach out to, assist with goals and tracking, and generally provide daily assistance. Although these interactions may not relate specifically to the user's goals, the content provided to a user and data obtained from the user in this manner can be used to carry out and update the management plan.

The data the server system 310 obtains can directly affect which interventions or interactions are provided, which programs are active and to what extent (e.g., what levels are set for the programs), the assessment of various risk levels (e.g., for physical or psychological conditions), and so on. In many cases, simple recommendations or questions by the server system 310 can be targeted directly to alleviating symptoms or risks occasioned by current or former cancer status. For example, when the server system 310 detects data indicative of anxiety or low energy, the server system 310 can provide an indication of the current weather and encouragement to visit a nearby state park. The rules of one or more programs may take into account that sunshine and physical activity are likely to address symptoms of depression anxiety or low energy. In fact, through analysis of symptom levels and activities of other patients at a similar stage of cancer treatment or survivorship, the server system 310 can set or adjust rules specifying when this suggestion should be provided.

In addition, the system may obtain information in ways that do not require explicit entry of an answer to a question. For example, if the system provides a content for user, the system can assess whether the user completes viewing the content, which areas the user spends the most time viewing, which links are selected, and so on. These can provide valuable information that indicates a user's level of engagement, mood, etc. Similarly, a user's performance in a game may indicate the user's reaction time, language capabilities, mood, and so on.

The server system 310 may cause many different types of interactions and digital therapeutics interventions to be provided to a user. For example, the system 310 can cause a device to perform any of the following actions: prompt a user to provide a journal entry or to view a prior journal entry; record a measurement from one or more devices; provide a survey or question for a user to answer; provide content for a user to read or view; initiate a challenge for a user with a defined time frame (e.g., a daily, weekly, or monthly challenge goal or competition); prompt a user to set, adjust, or view a personal goal; communicate with family, friends, or others regarding a user's goals or status; and initiate a call, message exchange, or real-time text chat with a health service provider. The actions taken by the system can provide educational information and activities to improve a patient's knowledge. The actions can provide motivation or encouragement to increase positive behaviors or decrease negative ones, for example, prior to a user performing a desired action. The actions of the system can reinforce positive behaviors, for example, by providing positive messages, rewards, or activities after a desired behavior is performed. These and other actions of the system can be performed as directed by the digital therapeutics programs that are active for the patient, with each active program potentially providing different interactions at different times. The interventions of the programs can be tailored to achieve any of various results, including adherence to a clinical regimen, behavior change, patient education, and so on.

In general, the system 300 can be used to provide a variety of digital therapeutics, which are not limited to supporting cancer patients and cancer survivors. For example, a few of the diseases or disorders that the system 300 can be used to treat include heart disease, diabetes, lung disease, immunological disease, mental disorders, chronic pain, and bone disease. While users with these conditions have needs that are different from those of cancer patients and cancer survivors, they can nevertheless benefit from the adaptability and total-body wellness support that the system 300 can provide. Similarly, the system 300 can provide support over any and all of a continuum of care, for example, prevention, diagnosis, treatment, and post-treatment.

Figure 4:
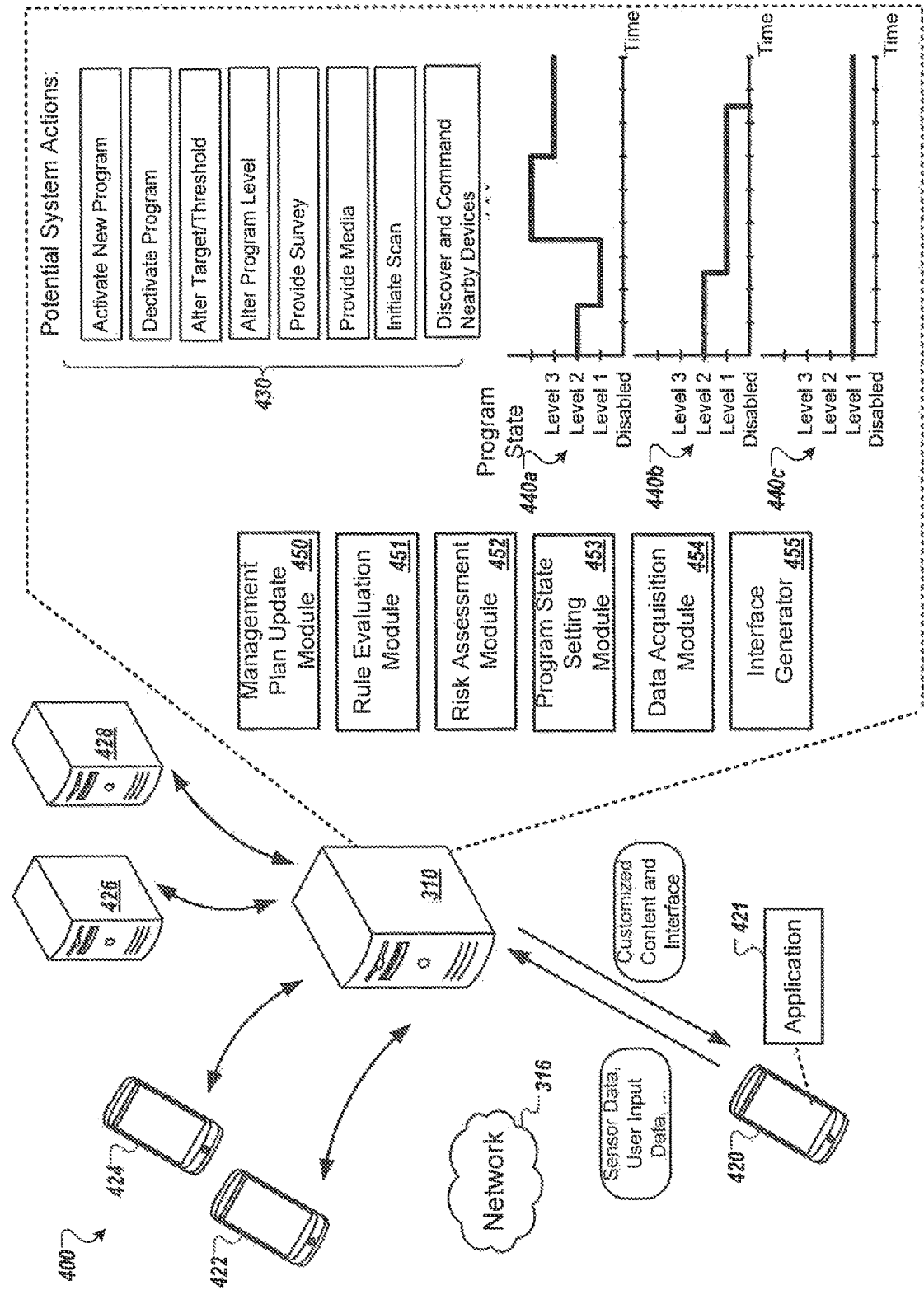
FIG. 4 shows an example of a system for generating an operating plan.

FIG. 4 shows an example of a system 400 for providing a digital action management plan. As discussed further below, the server system 310 is able to adjust and adapt the management plan for a device or the device's user, and also provide direct interventions and supports to encourage achievement of the goals of the management plan.

In the example of FIG. 4, a user has a mobile device 420. The device 420 or its user has previously been enrolled to a management plan by an administrator. Mobile device 420 has an application installed that helps carry out the interactions and interventions of the management plan. For example, the application 421 may collect sensor data and user input from the device 420 and other devices nearby on an ongoing basis. The application 421 provides this data to the server system 310 for storage and analysis. As the server system 310 applies the appropriate rules and programs of the user's management plan, the server system 310 periodically sends customized content and interface data to the mobile device 420 to be displayed through the application 421 or interacts with the mobile device 420 in another manner.

In general, the management plan can push content to the mobile device 420 for display as triggered by the rules of the various programs active in the management plan. Rather than the user manually requesting content, e.g., by opening the app to navigate to a web page, the server system 310 and/or the app 421 can initiate intermittent and unexpected interactions throughout the course of a day, week, etc. In a sense, the interactions of the management plan can be generated through a kind of always-on or continuous analysis by the server system 310. The programs of a management plan can provide contextually relevant interactions at any time, as determined appropriate by the server system 310 from the various data sources available to the server system 310.

The server system 310 communicates with the mobile device 420 over the communications network 316. To carry out the management plan, the server system 310 may also communicate with various other devices and third-party systems.

The server system 310 also interacts with third-party systems, illustrated as computing systems 426 and 428. These systems 426 and 428 represent any of a variety of public and private data sources. Additionally, the systems can represent sources for other data, such as weather data, environmental data such as pollution levels, upcoming events data, map data, and so on.

As a result, the server system 310 may interact with a first device, e.g., device 420 having a user. The system 310 can also interact with a second device associated with a service provider. The system can also interact with a third device, e.g., device 422 or device 424, associated with another user, such as a co-worker, friend, family member, etc.

With input collected on an ongoing basis from these data sources and others, the server system 310 applies the rules of each active program in the user's management plan. These rules can specify various different system actions to be performed. The server system 310 can administer programs and evaluate rules using any of the techniques discussed in U.S. Pat. No. 9,848,061, filed Dec. 19, 2017, and/or U.S. Pat. No. 9,753,618, issued on Sep. 5, 2017, both of which are incorporated herein by reference.

The incoming data stream regarding a device user, compiled from all available data sources, may be used to form a current data set or profile for the device or user. The server system 310 continuously update the profile representing the current status of the device or user, using all of the various input data sources.

Among the various actions that the server system 310 can perform are actions that alter or adjust the combination of programs in a management plan and the program state or level of individual programs. For example, the server system 310 may evaluate the incoming stream of data about a device or user, and extract specific data types and measurements relevant to each program. The rules that are applicable at a given time can specify the types of data that are needed for a program. For example, of the rules of a program, only a proper subset of the rules may be applicable to the current level and segment of the program. The server system 310 can identify the set of data needed to determine whether the conditions and triggers of the rules in the subset are satisfied.

The different program states or levels of a program can represent different portions, configurations, or operating characteristics of a program. Accordingly, changing the program state for a program can cause the system to use a different portion, configuration, or operating characteristic. In general, different program states may correspond to different levels of magnitude or frequency for changing operation of a device. Different program states may also cause the program to use different sets of content to provide to a device, or may use or different sets of rules to determine when and how to adjust operation of a device. Similarly, different program states may alter application behavior in various ways, such as by altering the level (e.g., type, magnitude, or frequency) of interaction with a user, or altering the types of options that are presented to a user on an interface of a device. In some implementations, different program states may correspond to different levels of targets or goals for the performance of a device or user. For example, at a first level or program state, a modest target is set, with more aggressive goals being set for other program states representing a need for a greater magnitude of change, or a greater urgency or frequency of making changes. In a similar manner, different program states may set different thresholds or triggers for device operation, and/or may cause different code of the programs to be used or cause different instructions to device to be generated.

Each program may have, in its corresponding set of rules, one or more rules setting conditions and triggers for altering a program state. These factors may be unique to each program, and to each level transition. That is, a first program may have different sets of rules that govern whether to transition from level 1 up to level 2, from level 2 up to level 3, from level 3 down to level 2, and so on. In some instances, changes in program state may occur at any time that appropriate conditions and triggers are met. In other instances, changes in program state may occur at transitions between segments or at other specified intervals.

In the example of FIG. 4, charts showing program states over time are shown for three different programs 440*a*, 440*b*, and 440*c* in the management plan for a device or user. The program states vary over time due to the server system 310 determining that more or less intervention is needed for corresponding topics at different times. The transition decisions are made based on rules of the programs applied to the current status profile for the device or user at the specific point in time when those transitions were made. As illustrated, the state of the first program 440*a* varies significantly over time. This may represent for example, variations for a power management program responding to highly variable loads experienced by a device. The second program 440*b* shows a gradual decrease from level two, to level one, and then disabling the program. This may represent, for example, steady progress of the device in managing a resource, such as communication bandwidth, to the extent that the rules of the program specify that no further monitoring is needed. The third program 440*c* represents a constant level over the time period. This may indicate, for example, that a device or user is maintaining acceptable performance, but may not be meeting target performance levels sufficiently to reduce the level.

The programs can be interdependent. The state of any given program may depend on the state of one or more other programs, or even all other programs in the management plan. Various techniques may be used to provide this interdependence. For example, program rules that specify system actions to be performed under certain conditions may specify that certain states of certain programs are a condition or trigger for a level transition. Similarly, the act of making a program active in a management plan or transitioning to a different level of a program may be a condition or trigger.

As another example, the output of a program may be used to set levels/program states of other programs. For example, the server system 310 can assess the types of survey questions or data types that programs use. Each program may include a specification of data types that are assessed using the program, or the specification can be inferred from the rules of the program. If a program is disabled but has a specification indicating data types that match those being requested by other programs, the disabled program may be activated. In some instances, analysis of output by a device or the results of some of the various programs, and data input requests of other programs, can be used to determine a relevance score between current a current state of a device or user and the other programs. When the relevance score satisfies a threshold, this may trigger the activation of a program or an adjustment to the level of a program.

In some implementations, relationships between programs may be predetermined, e.g., manually defined or explicitly set through rules. This is not required, however. Indeed, the analysis of the combined program states in a management plan and/or the outputs of the programs to a user can be effective to adjust program states even with no specific knowledge of interconnections between the subject matter of different applications/programs. The server system 310 can infer relationships through commonalities in program specifications and outputs of the programs. That is, the patterns of outputs of a program and requests for inputs by the program can show over time in the manner in which the program relates to other programs. The server system 310 may analyze these relationships, for example, comparing which segments of programs and which levels of programs relate to specific levels and segment of other programs. The system 310 can also apply machine learning techniques, such as reinforcement learning, to patterns of management plan creation, level transitions over time, and other factors. With a sufficient data set generated from the progress of many users, the server system 310 can identify typical patterns in user status profiles, with the corresponding combinations of programs and levels. As the system 310 assesses program state transitions over time, the server system 310 is able to identify combinations of programs and levels that produce the best results for users with specific backgrounds. For example, the server system 310 may identify, for each of multiple different cluster of negative outcomes or undesired states, which combinations of programs, and at what levels, are most effective at reducing the negative outcomes or undesired states over a time period, e.g., a week, a month, a year, etc.

For example, the server system 310 may evaluate user status profiles and corresponding program states over a period of time, and determine that users that have three particular programs active simultaneously have the highest likelihood of achieving a decrease in the level of a fourth program. From this determination, the server system 310 may generate rules that activate the three programs together if the fourth program is active. More complex conditions may be set if desired. For example, rather than activate all three programs, the change may be limited to activating only one of the programs if two of the three are already active and the fourth is also active. As another example, all three programs in the group may be activated if the level of the fourth program is above a threshold, but not if the level of the fourth program is below the threshold. Of course, the behavior learned of the server system 310 does not need to be expressed in explicit rules and can, in various implementations, be incrementally learned as part of a training state of a classifier, neural network, or other machine learning model.

In general, the server system 310 can use a variety of interactions, measurements, testing, feature vectors and stated or observed behaviors of a user to set program states. The server system 310 can use these same factors to select which digital management plan to use for a device, and when and how to provide instructions that alter the operation of the device. In addition, the server system 310 can identify digital state markers and use them as indicators for selecting certain management plans.

The server system 310 may evaluate various data sets to determine which combinations of data about a device or user constitute a digital state marker that is predictive of certain outcomes, whether desirable or undesirable. These digital state markers may represent markers for future performance of a device or user. As another example, digital state markers can be predictive of future outcomes for a device or user. For example, the server system 310 may access data sets for longitudinal studies that show data collections describing many devices, their characteristics, and outcomes over time. From analysis of this data, the server system 310 can select combinations of characteristics and actions that satisfy a minimum threshold of relevance to different outcomes, and define the identified combinations of data factors as digital state markers. As a result, the system may detect combinations of program states that serve as a digital state marker for positive outcomes (such as a device's efficiency, output quality, long uptime, high responsiveness, maintained security, etc.) or for negative outcomes (e.g., virus infection, insecurity, bandwidth bottlenecks, overheating, etc.).

In some implementations, digital state markers can be defined in terms of digital operating programs and their states. As an example, the digital state markers can be combinations of program states that govern operation of a device, and represent at least a minimum likelihood of a particular event occurring for the device within a certain time frame (e.g., device failure within one year with at least an 80% likelihood, or running out of battery power in the next 30 minutes). Accordingly, the server system 310 may define these combinations of programs and states as feature vectors that may be used to alter the combination of states, for example, to add a particular additional program to reduce the risk of a negative outcome, or increase the likelihood of a positive outcome. The digital state markers may also optionally be defined in terms of (i) combinations of program states concurrently active at a time plus (ii) one or more attributes or conditions of a device or user. For example, one combination of program states may not represent a marker for a certain outcome on its own, but that combination may be considered a digital state marker when combined with certain detected properties of a device (e.g., battery less than 25% and CPU usage consistently above 50%, or a certain device model and device age).

The server system 310 performs a variety of functions in creation and administration of the dynamic, customized management plans. A few of these functions are represented in FIG. 4 as various modules of the server system 310. While the various functions are illustrated separately for clarity in illustration, various implementations may combine these functions into a single module for a different grouping of modules.

Figure 5:
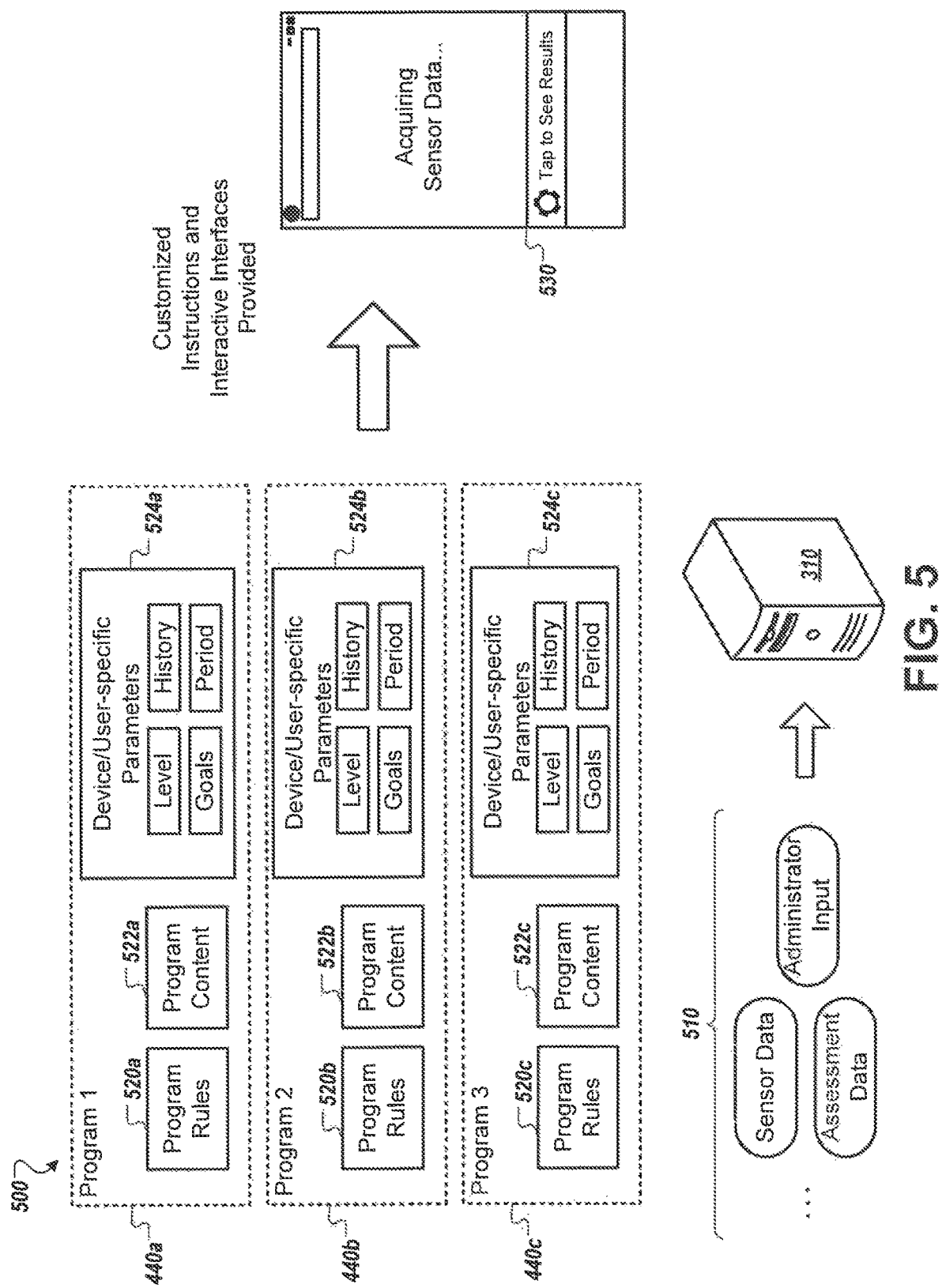
FIG. 5 is a diagram that illustrates examples of data used to generate dynamic, customized operating plans.

A management plan update module 450 can modify the management plan for each individual user, for example, based on changes in status of the device or user, or manual entry from an administrator through the portal discussed for FIG. 5.

A rule evaluation module 451 can select, from each active program of a management plan, the appropriate rules corresponding to the current segment and level of the program. Then, the rule evaluation module 451 compares aspects of the status profile of the device or user with the triggers and conditions of the selected rules. The rule evaluation module 451 causes the system actions corresponding to rules with satisfied triggers and conditions to be performed.

A risk assessment module 452 can determine the unique risk profile for a device or its user given the current profile and historical data. Because the server system 310 collects and stores information for numerous environmental and historical factors, the server system 310 can calculate the customized risks based on the data set compiled for the device or user. To aid in generating these risk levels, the server system 310 may store and access data sets representing outcomes and statistics representing many different groups of people. From clinical data and statistical analysis of the data sets, the server system 310 can determine a baseline risk level as well as a large set of factors that increase and decrease risk. The server system 310 identifies which of the many factors are applicable given a user's current profile and historical data and adjusts the baseline risk accordingly. In this manner, risk levels can be generated for many different conditions.

The risk assessment module 452 can determine a device's or user's risk with respect to a set of potential outcomes and update those as the person's profile changes. Similarly, as the server system 310 receives new assessment data or as outcome patterns are observed for the device and users affected by management plans of the system, the risk levels are also changed. The risk levels determined by the risk assessment module 452 may be used in a number of ways. In some instances, a person may be informed of their risk level and how it compares to other user. As another example, the risk levels may be provided as input to the rules of various programs, provided as input to the rules of various programs, which may condition they performance of certain system actions on risk levels in certain ranges. For example, a risk level for reduced mobility may be calculated and provided as an input to a program for physical exercise, which may increase or decrease its level based on that risk level. Risk levels for a user may trigger the activation of a program or increase in the level of a program, e.g., if the user's risk of experiencing an associated condition is above a threshold. Similarly, risk levels can trigger the deactivation of a program or decrease in the level of a program, e.g., if the user's risk is below a threshold.

The program state transition module 453 may govern transitions in program state for a person's management plan. As discussed above, changes may be made due to the interaction and execution of rules for different programs. In addition, or as an alternative, a module of the system 310 may be used to manage these changes. This module 453 may initiate changes in programs based on analysis of a user status profile and current and previous program states for the user. The program state transition module 453 may limit or normalize changes indicated by program rules. For example, the program state transition module 453 may enforce certain restrictions, such as limiting a frequency of level changes that are allowed over a period of time. An advantage of using the program state transition module 453 to initiate program state transitions is the ability to apply analysis for the management plan as a whole, rather than just as the rules of a single program within a management plan. As a result, the program state transition module 453 can enforce various aspects desired for management plans, whether determined using manually set rules, administrator preferences, relationships learned through analysis of stored data, and so on.

The data acquisition module 454 coordinates the requests for information from devices 420, 422, 424, 426, 428, and others. This data acquisition module 454 may obtain a list of requested data types or questions from the various programs, assess them to condense into a final set of needed information, and schedule interactions to acquire the needed data. Similarly, the data acquisition module 454 may periodically request sensor data, weather data, and any other applicable type of information needed from various systems to allow the rules of the programs to be evaluated.

An instruction generation module 455 produces data packages that are sent to the application 421 on the mobile device 420. The instruction generation module 455 specifies content to be provided on the user interfaces of the application 421, which may include various combinations of media, text, data entry elements, and so on. When a module specifies that certain content should be provided, the interface generator 425 receives the indication, determines the content layout formatting and so on that are needed. Through the interfaces that are generated, the system provides many different types of interactions with users. For example, the programs and other elements of the system 310 may cause a survey to be provided, provide media to the user, provide instructional materials, provide a test, provide a game, or initiate other activity with the user. Further, the instruction generation module 455 can specify interactions beyond interactions with a visible display. Interactions can be specified to involve audio output, voice input, haptic output, gesture input, and other input/output modalities.

FIG. 5 shows additional data that the server system 310 can use to generate dynamic, customized management plans. The figure shows three programs from FIG. 4, with an indication of stored data and user-specific parameters for each.

Each program includes a set of program rules 520*a*, 520*b*, and 520*c*. The overall set of rules for a program are generally applicable to all users of the program. However, as discussed above, different subsets are applicable to different users at different times. Further, of the applicable subset of rules, only certain rules will have their conditions and triggers satisfied at any given time. Rules may be marked with metadata or may include elements specifying which levels and segments of a program each rule corresponds to. This can allow the server system 310 to filter, for each user, the overall set of rules for the program to a smaller subset to actually evaluate for the user. This can greatly increase efficiency and reduce computation, especially when the server system 310 supports a very large number of devices or users simultaneously.

Each program includes a set of program content 522*a*, 522*b*, and 522*c*. This content represents source material from which customized interactions with a user are generated. For example, the content for a program may include questions, videos, audio segments, images, instructional materials, messages (e.g., indicating encouragement, reminders, etc.), games, and other content. When indicated by the program rules 520*a*, 520*b*, and 520*c*, specific portions of the content may be accessed, combined into a data package for the user, and provided by the server system 310 to the mobile device 520 for presentation to the user.

Each management plan includes device-specific or user-specific parameters 524*a*, 524*b*, and 524*c* for each program. This does not mean that the set of parameters is unique among all users and devices; rather, each user or device has a separate set of parameters (e.g., program levels and segments) that are separately stored and adjusted, and so are specific to that device or user. The parameters can include the current level of the program, current targets or goals for the program, historical information for the device or user, and an indication of the current period or segment that is active in the program. In general, segments can represent to different sequential periods of time, in which the content or interaction of a program with a device may change. The device-specific or user-specific parameters 524*a*, 524*b*, and 524*c* specify how the programs 440*a*, 440*b*, and 440*c* process the input data 510, and ultimately how the customized instructions and interactive user interfaces 530 are determined.

The level can represent a level of need or intensity of needed interaction for the topics or categories of that program. Thus, a higher level may indicate more severe need for monitoring or interaction while carrying out the management plan. This is optional, however, and levels may have a different meaning. In some instances, a high level may indicate greater progress, for example, goals in an advanced range, achievement of certain skills, or other positive attributes.

The server system 310 is also shown receiving a set of input data 510. This input data 510 can be used to determine the current status of a device or user, or historical information about the device or user. Input data can be actively requested by the server system 310 from a device, another server system, or another device than the one associated with the management plan. Input data can also be passively received, e.g., periodically sent or broadcasted by other devices. As discussed above, the input to the server system 310 can include may different sources including sensor data from a mobile device or other devices, assessment data (e.g., survey responses, test results, etc.), input from administrators, weather data, points of interest data, or environmental data, data from a wireless wearable device, to name a few. Other types of data used by the server system 310 in carrying out the programs 440a, 440b, and 440c and adjusting the states of the programs 440a, 440b, and 440c is discussed with respect to FIG. 8.

Figure 6A:
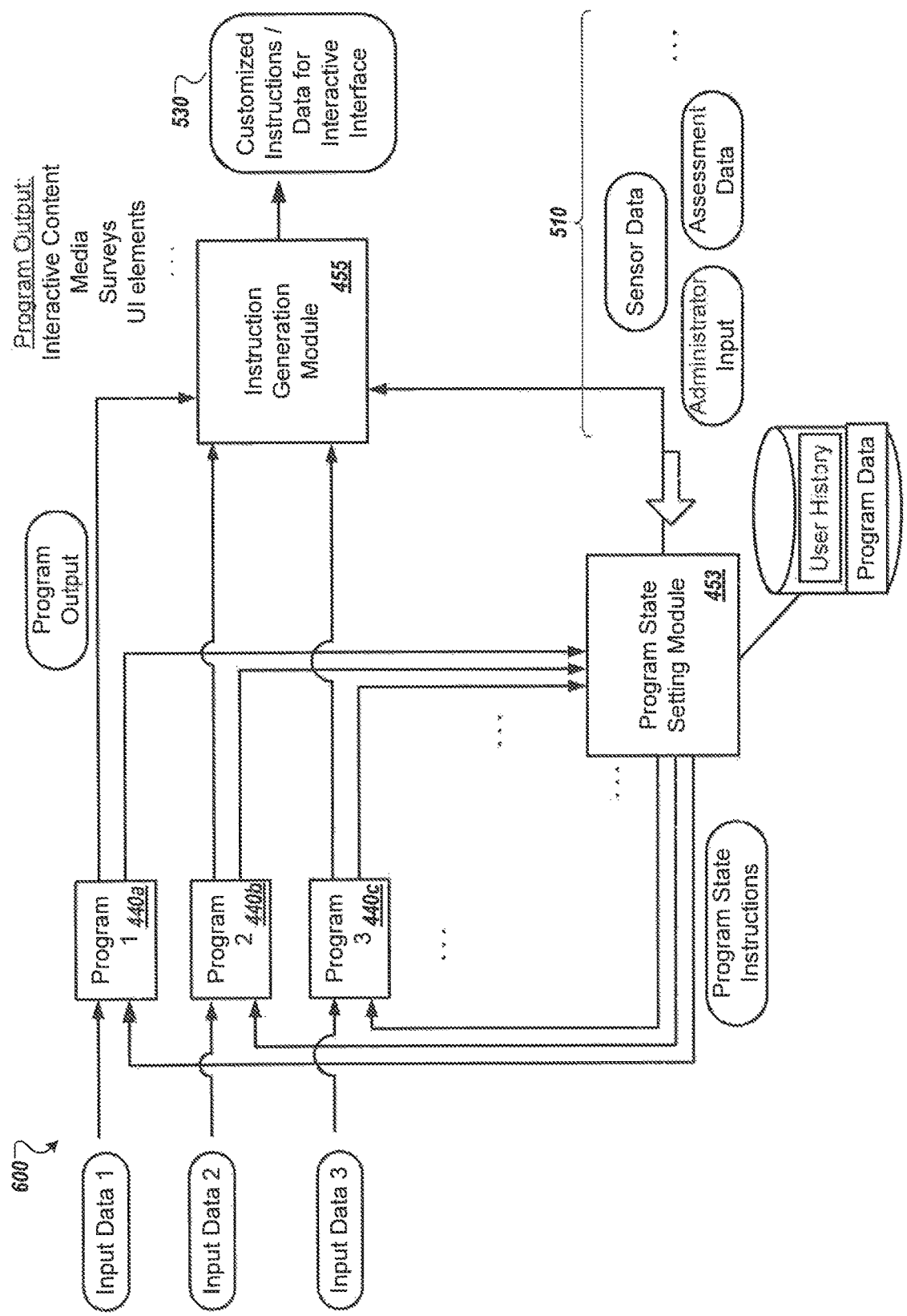
FIGS. 6A and 6B are diagrams that illustrate examples of techniques for adjusting states of operating plan programs for devices in complex systems.
Figure 6B:
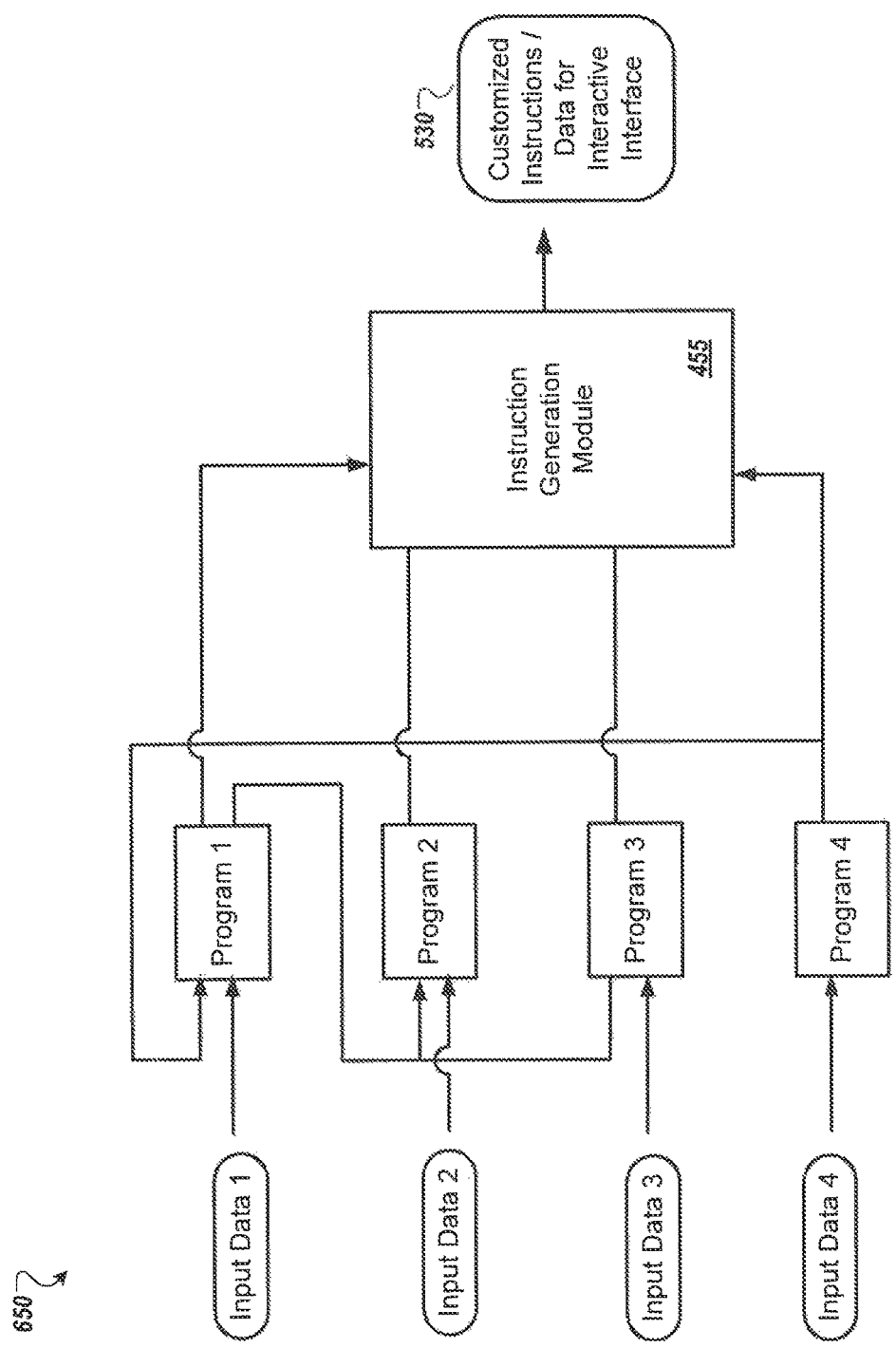

FIGS. 6A and 6B are diagrams that illustrate examples of techniques for adjusting states of digital operating programs.

FIG. 6A shows an arrangement 600 of elements in which each of various programs 440a, 440b, and 440c receive an input data set used to evaluate their corresponding rules. These data sets may be the same for each program or different for different programs. In addition to receiving the input data representing a current status and historical information for a device or user, each program receives a signal from the program state setting module 453. The module 453 assesses input data 510 which may include any or all of the information used by the programs 440a, 440b, and 440c. The module 453 issues program state instructions which can dynamically change the level or state of each program as the module 453 determines appropriate.

As the programs provide output to the instruction generation module 455, the output of the programs is also provided to the program state setting module 453. The output can represent messages to be provided, questions to be asked in a survey, interactive activities of the application, indications of media provided to the user, and so on. The module 453 may analyze these program outputs and use the analysis results to change the current levels of the programs. The program state setting module 453 can analyze the outputs of the various programs in a number of ways. For example, the module 453 may extract text from questions or messages initiated by the programs, and map keywords and phrases in the extracted text to different topics. Other mappings may indicate relationships between topics and programs, allowing output of one programs to be assessed for relevance to other programs. Sentiment analysis can also be performed on the outputs of the programs, allowing the module 453 to determine, for example, whether conditions are improving or worsening. The module 453 may also assess the frequency of activity of each program, for example, determining whether a program is initiating communication with increasing or decreasing frequency, and take this into account in assessing which programs and levels are likely to be needed.

The module 453 also receives data indicating the current level and segment that is active for each program, and this data also is used by the module 453 to update the levels of the programs. As shown in FIG. 6A, the program state setting module 453 may use information from any or all of the programs to set the state of any or all of the other programs. From data indicating the progress of various users over the course of using a management plan, the program state setting module may infer which combinations of program, program levels, and even specific segments of programs are most effective at assisting users. This analysis may be done across a variety of dimensions. For example, different groups may be assessed by age, location, physical activity levels, online activity, and many other factors.

For each of the various permutations of characteristic combinations, and other factors, the server system 310 may identify examples from its data set that represent the same or similar combination of aspects. Then, with information about how devices or users have progressed with different combinations of programs and levels active, the server system 310 can assign likelihood scores indicating, for example, a probability that each level of each program is to achieve a desired result, such as reduction of a negative outcome. The same analysis may be done to determine scores for different combinations of programs and levels. These likelihood scores may be used directly by the program state setting module 453. As another example, the likelihood scores may be assessed by the server system 310 to define rules that the program state setting module 453 applies to automatically initiate changes in program states.

In some implementations, the server system 310 may determine the specific set of factors experienced by an individual at a given time, and identify examples of users having the same or similar factors, based on databases of information maintained by the server system 310. The server system 310 may thus define, at various times, custom data sets from historical information about other users to determine a user specific likelihood of desired outcomes for the user's current situation. These user-specific measures may be used by the program state setting module 453, along with user-specific risk levels discussed above, to adjust program states.

FIG. 6B shows another example 650 of automatic transitions between program states. By contrast with FIG. 6A, a predetermined set of connections is used between the programs. For example, program 1 has its state adjusted based on the output or state of program 4, but the decision does not take into account the output of or state of program 2 and program 3.

In addition, rather than including a centralized program state setting module 453, the rules of each program set the state of the program or another program. For example, program 4 may include rules that adjust the level of program for based on the input data to the program, which may indicate historical information about the user. Program 4 may also provide a signal to program 1 indicating that a level of program 1 should be changed. Alternatively, the level of program 4, or outputs to be provided to the user from program 4, maybe provided as input to program 1 and used to adjust program 1 according to program 1's own rules.

Figure 7:
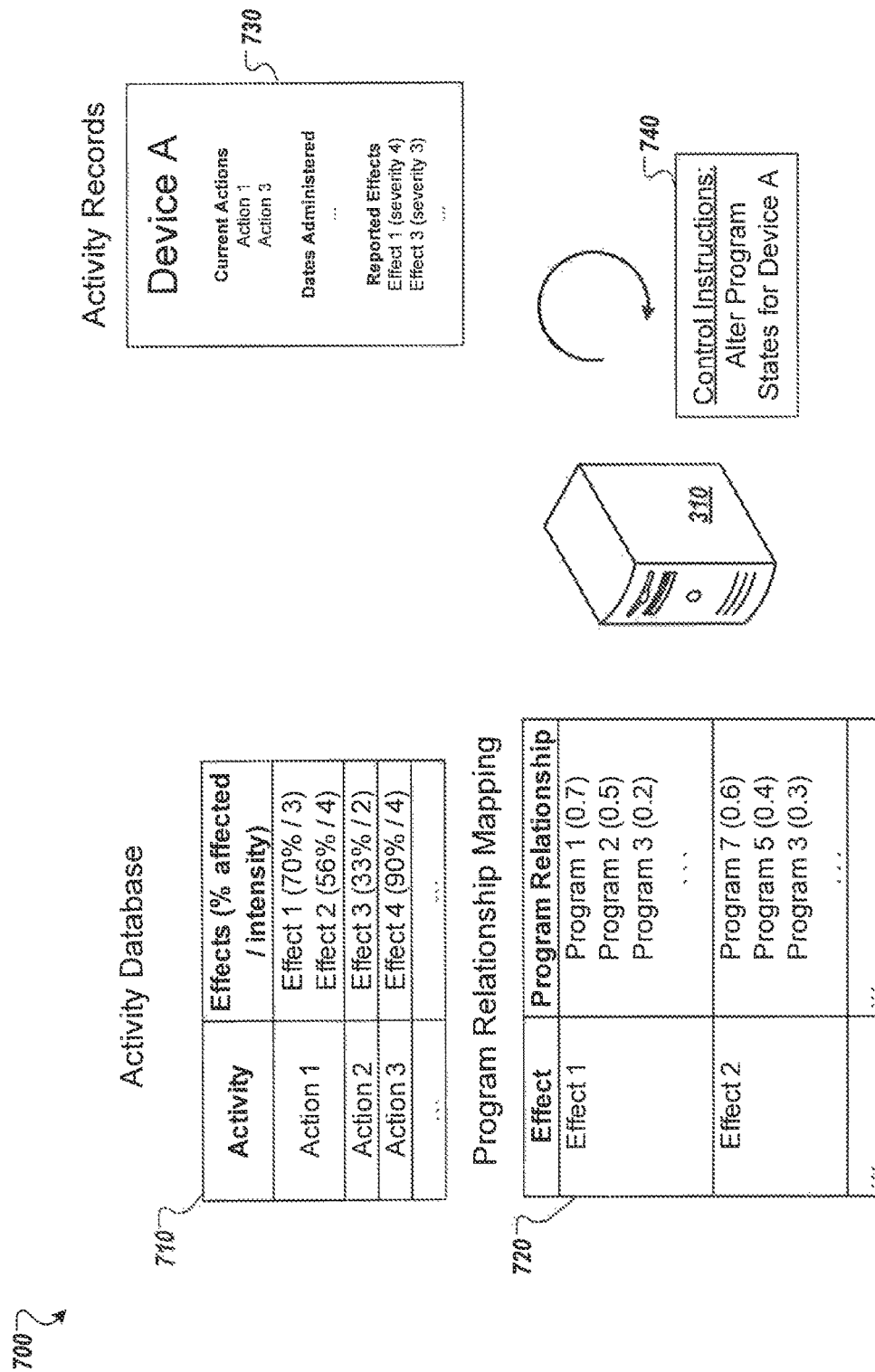
FIG. 7 is a diagram that illustrates examples of using activity information to develop an operating plan for devices in complex systems.

FIG. 7 is a diagram that illustrates examples of using activity information of the device or user. The server system 310 can store information about various activities or actions, as illustrated by database 710. As examples, actions can be indicated by information such as a name, category or type, etc. Scores indicating the severity of the effect, e.g., an average measure for those who do experience the effect, can also be indicated The server system 310 can also store a mapping 720 indicating relationships between the effects of actions and different programs. For example, for a given action effect, scores may be provided indicating a degree of relevance to different programs. The score may represent a relevance of the program or a degree to which the program can address the effect. The scores in the mapping 720 do not need to be based on intuitive relationships, however, and may be determined through analysis of activity data tracked over time or through historical outcomes of users of the system. In particular, the scores can be determined for different outcomes based on the occurrence of certain digital state markers, or for certain progressions or transitions between digital state markers over time. The scores may be manually defined in some instances. In another example, programs for devices such as sensor data have a score in the mapping that relate to battery life and pulling sensor data, and a low score for relevance to results of pulling the sensor data. Different programs can have many effects: a high level of sensor monitoring can decrease battery life and available computing resources such as CPU or RAM.

The server system 310 also stores activity records 730 for each device or user. These records 730 can indicate current actions or a current state of the device or the user as well as historical information about actions of a device or user. The records 730 can indicate a variety of metadata or contextual information about how and when the actions were assigned. In addition, actual effects or conditions that the device or user experienced can be specified, as reported by the user directly through a mobile device, or through sensor data.

Using the device or user's action records 730, and the indications of which actions were taken when, the server system 310 can look up in the action database 710 which action effects are likely for the device or user. In addition, the server system 310 can use the mapping 720 to determine which programs (and potentially specific levels and segments of the programs) are most relevant to the likely effects. Given a likely effect predicted using the action records, or from actual effects indicated by the action records, the server system 310 identifies the relevance scores for one or more programs. The server system 310 may then combine the scores across different effects.

For example, all effects of current actions of a device or user and former actions of a device or user can be determined. The scores in the mapping 720 are determined for each of these effects. Then, for each program, the relevance scores may be combined by weighting the values. Scores corresponding to likely effects may be weighted or discounted according to the likelihood from the action database 710. Similarly, scores for effects estimated from actions that are not current may be discounted in some instances based on how long ago the corresponding action was administered. Similarly, scores can be weighted by the typical intensity of the effect. By contrast, for actual effects experienced by the device or user, the scores from the mapping 720 may not be discounted, or may be increased. The weighted scores for a program may then be added or otherwise combined to give an overall measure of the likely relevance of the program given the current state or actions and history. The combined scores for the program are then compared to a threshold, and if the score satisfies the threshold, the corresponding program may be activated or have its level increased. The same technique can be used for each of the programs available.

With these techniques, the system 310 can activate digital operating programs to address the actual effects experienced and/or sensed by a device or user. The system 310 can also activate programs to address potential effects that may be likely but may not be reported, or may be developed in the future. The server system 310 can generate control instructions 740 that specify specific programs to activate, deactivate, or change in level based on the analysis of the device's or user's activity records 730, and based on the other information discussed above.

In some implementations, management plans can be provided to manage the operation of a device to improve a user's behavior or health. For example, a server-based management system can use various programs to customize instructions to a mobile device of a user, such as a user's cellular phone or smart watch. The management plans can support various aspects of a user's wellbeing, such as physical, emotional, social, and mental health. Just as different programs may focus on different aspects of a devices operation (e.g., different programs for battery life, wear and component lifespan, thermal management, etc.), different programs may monitor and provide interventions to improve different aspects of a user's health (e.g., different programs for nutrition, exercise, sleep, smoking cessation, etc.). In some instances, individual programs or combinations of programs may be specialized for treatment or management of specific health conditions, especially long-lasting or chronic conditions such as diabetes, cancer and cancer survivorship, heart disease, arthritis, etc. The systems and methods of the present application can optionally perform or be combined with the techniques disclosed in U.S. patent application Ser. No. 15/803,556, filed on Nov. 3, 2017, which is incorporated by reference herein.

Some management plans for a user can assist a user to reach a goal such as losing weight, increasing sleep quality, creating a healthy habit, and so on. These user behaviors and outcomes that are affected are not merely behaviors interacting with devices, but often represent changes in real-world aspects of the user's life outside of human-device interaction. The management plan for a particular device and user, and the timing for delivery of instructions causing presentation of different content by the particular device to the user, are dynamically selected and updated using a series of different digital operating programs that can address different aspects of a user's wellbeing. As discussed below, each program can have separate sets of content, rules, assessments, and interventions for providing a customized, adaptive experience for a user. The system can operate in an "always-on" manner, frequently or continually assessing a data stream indicating the user's current status and context, and providing targeted interactions that are relevant to the user's current or estimated future needs.

Thus, the management plans can be applied to manage the operation of devices, whether a user's personal mobile device(s) or a medical device, to provide digital therapeutics or other therapy to treat health conditions or improve health. In use, the server system (e.g., server system 310 of FIG. 3) may identify and provide management plans that decrease unwanted risks and increase likelihoods of improving a desired area of the user's life. For example, the predetermined set of programs that the server system 310 uses to generate a management plan can be digital therapeutics programs. The programs and levels set can specify areas of the user's wellbeing to support, e.g., with different programs selected from among programs for nutrition, sleep, exercise, weight management, alcohol use, smoking cessation, anxiety management, depression management, sexual health, pain management, fatigue management, psychosocial health, adherence to physician instructions or treatment regimens, etc. The combination of the different programs, at the user-specific levels set and varied as discussed above, can instruct the user's device to provide a variety of interactions and interventions that can help change a user's behavior and actual health outcomes. These interactions can include, for example, suggestions for behavior change, alerts, reminders, games, educational information, surveys, media, social media interactions, real-time communication, and so on.

As a result, a management plan can be used to provide precision medicine to different people. The specific interactions for any given person can be custom selected based on the device-specific or user-specific set of program states indicted by the management plan. Similarly, the timing and content of interactions over the course of a precision medicine therapy are customized using the periodic or ongoing data stream that the server system 310 receives which indicates the behavior, physical characteristics, or other attributes or actions of the user. For example, even when a certain type of interaction, such as a reminder or instruction to a user, is determined to be appropriate for a user, the time, location, and form of the presentation (e.g., text, image, video, audio, interactive game, real-time call to another person, etc.) may be initiated by the server system 310 just in time, as triggered by rules or other logic of the digital therapeutics programs.

The precision medicine provided by the system to an individual can be based on data from genomics, pharmacogenomics, proteomics, metabolomics, multi-omics, and other analysis techniques for an individual. The changes to device operation that the management plan causes can be configured to cause interactions with the user that address any of a variety of health conditions, both physical and mental, such as diabetes, cancer, heart disease, kidney disease, anxiety, depression, etc.

Initially, the management plan for a user can be set using a portal such as the portal 332 shown in FIG. 3E, and can be provided to an administrator, and in some implementations, to the user or to another user, such as a family member of the user, a friend of the user, and/or a service provider for the user.

In some implementations, all of the programs used to define a management plan or care plan for a user can be used to determine output of a single application on a single device, such as a user's phone. The programs and levels (e.g., program states) are adjusted dynamically, according to a combination of factors such as user inputs, user actions, and sensor data as discussed above. The level of a program may affect, for example, how frequently the program communicates with the user, how ambitious or difficult the goals and activities of the program are, how closely a person's behavior is monitored, and so on. Different levels may correspond to different levels of user need. For example, a motivation program may have a first level that helps a user monitor and understand their habits when they are trying to maintain a habit. A second level may provide more aggressive goal setting and motivation, with more frequent interactions to help the user develop a new habit. For example, the program may interact with devices for friends and family members to more actively assist in helping a user meet their goals. In some implementations, different levels of a program, may respond to different goals or conditions.

In many cases, simple recommendations or questions by the server system 310 can be targeted directly to alleviating symptoms or risks associated with the user's current status. For example, when the server system 310 detects data indicative of anxiety or low energy, the server system 310 can provide an indication of the current weather and encouragement to visit a nearby state park. The rules of one or more programs may take into account that sunshine and physical activity are likely to address symptoms of low energy. In fact, through analysis of symptom levels and activities of other users at a similar state, the server system 310 can set or adjust rules specifying when this suggestion should be provided.

In addition, the system may obtain information in ways that do not require explicit entry of an answer to a question. For example, if the system provides a content for user, the system can assess whether the user completes viewing the content, which areas the user spends the most time viewing, which links are selected, and so on. These can provide valuable information that indicates a user's level of engagement, mood, etc. Similarly, a user's performance in a game may indicate the user's reaction time, language capabilities, mood, and so on.

The server system 310 may cause many different types of interactions and digital therapeutics interventions to be provided to a user. For example, the system 310 can cause a device to perform any of the following actions: prompt a user to provide a journal entry or to view a prior journal entry; record a measurement from one or more devices; provide a survey or question for a user to answer; provide content for a user to read or view; initiate a challenge for a user with a defined time frame (e.g., a daily, weekly, or monthly challenge goal or competition); prompt a user to set, adjust, or view a personal goal; communicate with family, friends, or others regarding a user's goals or status; and initiate a call, message exchange, or real-time text chat with a service provider. The actions taken by the system can provide educational information and activities to improve a user's knowledge. The actions can provide motivation or encouragement to increase positive behaviors or decrease negative ones, for example, prior to a user performing a desired action. The actions of the system can reinforce positive behaviors, for example, by providing positive messages, rewards, or activities after a desired behavior is performed. These and other actions of the system can be performed as directed by the digital operating programs that are active for the user, with each active program potentially providing different interactions at different times. The interventions of the programs can be tailored to achieve any of various results, including adherence to a regimen, behavior change, user education, and so on.

For example, for a user who is trying to achieve a goal of increasing physical activity, location data indicating that the user is near an exercise class may trigger the system to provide, at that time, helpful information, such as a reminder of the user's current goal, praise for recent progress, or information about the class.

In some implementations, the management plan may include information about friends and family members of the user, and phone numbers, email addresses, device identifiers, or other information that enables the server system 310 to interact with them. For example, the server system 310 may communicate with a family member's device and friend's device, as just a few examples. Just as the server system 310 can provide occasional surveys or interactive activities to the user, server system 310 can also generate customized surveys and activities for friends and family of the user. These interactions can provide confirmation of data that the user provided, and/or different types of data, such as information that the user may not personally be aware of. The system can initiate communication with computing systems for the user's physician, insurance company, social media network, calendar provider, or other service also.

Each of multiple devices can run an interactive application that receives and carries out instructions from the server system 310. All of the device may receive surveys, educational information, and other interactive activities. For example, when information is needed, or when compliance with a goal needs to be verified, a friend or family member may be asked in addition to or instead of the user. In some implementations, friends or family members may remotely view some information about the user, including goals, progress toward goals, status information, and an indication of which programs are active. This information may be subject to consent of the user. A caregiver may be provided this same information as well as indications of levels of programs, recent interactions, and other data gathered by the system. The caregiver's interface through the application may further allow the caregiver to set goals or change the states of programs, while the interface for friends and family may not allow these changes.

In some implementations, relationships between programs may be predetermined, e.g., manually defined or explicitly set through rules. This is not required, however. Indeed, the analysis of the combined program states in a care plan and/or the outputs of the programs to a user can be effective to adjust program states even with no specific knowledge of interconnections between the subject matter of different applications/programs. The server system 310 can infer relationships through commonalities in program specifications and outputs of the programs. That is, the patterns of outputs of a program and requests for inputs by the program can show over time in the manner in which the program relates to other programs. The server system 310 may analyze these relationships, for example, comparing which segments of programs and which levels of programs relate to specific levels and segment of other programs. The system 310 can also apply machine learning techniques, such as reinforcement learning, to patterns of care plan creation, level transitions over time, and other factors. With a sufficient data set generated from the progress of many users, the server system 310 can identify typical patterns in user status profiles, with the corresponding combinations of programs and levels. As the system 310 assesses program state transitions over time, the server system 310 is able to identify combinations of programs and levels that produce the best results for users with specific backgrounds. For example, the server system 310 may identify, for each of multiple different cluster of symptoms, which combinations of programs, and at what levels, are most effective at reducing the symptoms over a time period, e.g., a week, a month, a year, etc.

For example, the server system 310 may evaluate user status profiles and corresponding program states over a period of time, and determine that users that have three particular programs active simultaneously have the highest likelihood of achieving a decrease in the level of a fourth program. From this determination, the server system 310 may generate rules that activate the three programs together if the fourth program is active. More complex conditions may be set if desired. For example, rather than activate all three programs, the change may be limited to activating only one of the programs if two of the three are already active and the fourth is also active. As another example, all three programs in the group may be activated if the level of the fourth program is above a threshold, but not if the level of the fourth program is below the threshold. Of course, the behavior learned of the server system 310 does not need to be expressed in explicit rules and can, in various implementations, be incrementally learned as part of a training state of a classifier, neural network, or other machine learning model.

In general, the server system 310 can use a variety of interactions, measurements, testing, biomarkers (e.g., physiological readings, blood test results, genetic information, etc.) and stated or observed behaviors of a user to set program states. The server system 310 can use these same factors to select which digital therapeutic interventions to provide to an individual user, and when and how to provide them. In addition, the server system 310 can identify digital biomarkers and use them as indicators for selecting certain digital therapeutics. Certain combinations of data about a patient's activities and lifestyle can indicate health status and health risks of a user, just as the user's blood chemistry, genetic profile, and other observable physical traits may indicate health status and health risks. Similarly, data that the server system 310 collects about a user's activities and preferences, in combination with information about physical traits, may serve as digital biomarkers that provide more accurate predictive information than the physical traits alone.

As an example, the server system 310 may define a particular biomarker to represent a patient having a certain gene or combination of genes, with a sedentary activity profile, and certain diet characteristics. This combination of factors may be known to provide increased risk for cancer or other health conditions. When a user is determined to have this combination of factors, which may be determined from digital records of sensor data, behavioral data, device interaction patterns, and so on, the server system 310 may input to the various digital therapeutics programs that the digital biomarker is present. The various programs may then respond with interventions tailored to alter the behaviors that cause the digital biomarker to be present, or to encourage other behaviors that decrease the risks associated with the digital biomarker.

The server system 310 may evaluate various data sets to determine which combinations of data about a user constitute a digital biomarker that is predictive of health outcomes. For example, the server system 310 may access data sets for longitudinal studies that show data collections describing many individuals, their characteristics, and their health outcomes over time. From analysis of this data, the server system 310 can select combinations of characteristics and actions that satisfy a minimum threshold of relevance to different health outcomes, and define the identified combinations of data factors as digital biomarkers.

In some implementations, digital biomarkers can be defined in terms of digital therapeutics programs and their states. For example, by analysis of users and their health outcomes, the server system 310 may identify combinations of programs and levels that, when active may represent certain risks, when taken alone or in combination with physical health traits. Accordingly, the server system 310 may define these combinations of programs and states as biomarkers that may be used to alter the combination of states, for example, to add a particular additional program to reduce the risk of a future complication. Digital biomarkers can be defined in terms of combinations of programs and program states, together with different combinations of physical, genetic, behavioral, or other traits. For example, a digital biomarker may represent a particular combination of program states in a management plan combined with certain physical traits and/or certain behavioral events or patterns detected over the course of the server system 310 administering the management plan.

An assessment module can determine the unique risk profile of a user given the user's current profile and historical data. Cancer patients and cancer survivors often have drastically different risk profiles compared to others. From one cancer patient or survivor to the next, the risks maybe similarly diverse. As an example, a patient that has undergone radiation therapy may have a higher risk of incidence of later cancers of other types. As another example, a breast cancer survivor may have a much higher risk of adverse health effects due to alcohol consumption then a person that has not had breast cancer. A person's lifestyle, exposure to environmental factors, genetic profile, family medical history, and many other factors result in unique risk levels for individual patients. Because the server system 310 collects and stores information for these factors, the server system 310 can calculate the individualized risks based on the data set compiled for the user. To aid in generating these risk levels, the server system 310 may store and access clinical data sets representing outcomes and statistics representing many different groups of people. From clinical data and statistical analysis of the data sets, the server system 310 can determine a baseline risk level as well as a large set of factors that increase and decrease risk. The server system 310 identifies which of the many factors are applicable given a user's current profile and historical data and adjusts the baseline risk accordingly. In this manner, risk levels can be generated for many different conditions, e.g., pain, depression, recurrence of cancer, reduced sensory ability, etc.

The assessment module can determine an individual's risk with respect to a set of potential outcomes and update those as the person's profile changes. Similarly, as the server system 310 receives new clinical data or as user outcome patterns are observed for the users of the system, the risk levels are also changed. The risk levels determined by the assessment module may be used in a number of ways. In some instances, a person may be informed of their risk level and how it compares to other cancer patients or survivors, or to other people in general. As another example, the risk levels may be provided as input to the rules of various programs, provided as input to the rules of various programs, which may condition they performance of certain system actions on risk levels in certain ranges. For example, a risk level for reduced mobility may be calculated and provided as an input to a program for physical exercise, which may increase or decrease its level based on that risk level. Risk levels for a patient may trigger the activation of a program or increase in the level of a program, e.g., if the user's risk of experiencing an associated condition is above a threshold. Similarly, risk levels can trigger the deactivation of a program or decrease in the level of a program, e.g., if the user's risk is below a threshold.

As discussed above, a program state transition module may govern transitions in program state for a user's management or care plan. As discussed above, changes may be made due to the interaction and execution of rules for different programs. In addition, or as an alternative, a module of the system 310 may be used to manage these changes. This program state transition module may initiate changes in programs based on analysis of a user status profile and current and previous program states for the user. The program state transition module 453 may limit or normalize changes indicated by program rules. For example, the program state transition module 453 may enforce certain restrictions, such as limiting a frequency of level changes that are allowed over a period of time. An advantage of using the program state transition module to initiate program state transitions is the ability to apply analysis for the care plan as a whole, rather than just as the rules of a single program within a care plan. As a result, the program state transition module can enforce various aspects desired for care plans, whether determined using manually set rules, administrator preferences, relationships learned through analysis of stored data, and so on.

The program state setting module 453 also receives data indicating the current level and segment that is active for each program, and this data also is used by the module 453 to update the levels of the programs. As shown in FIG. 4A, the program state setting module 453 may use information from any or all of the programs to set the state of any or all of the other programs. From data indicating the progress of various users over the course of using a care plan, the program state setting module may infer which combinations of program, program levels, and even specific segments of programs are most effective at assisting users. This analysis may be done across a variety of dimensions. For example, different groups may be assessed by symptoms experienced, intensity of symptoms, type of cancer experienced, stage of cancer or length of time in remission, types of treatments used, types of medications currently administered or previously administered, age, location, nutrition choices, physical activity levels, and many other factors.

For example, the server system 310 may determine that for a breast cancer survivor currently experiencing fatigue one year into remission, a certain set of programs and levels provides a high likelihood of reducing the fatigue. Similarly, the analysis may show that a different set of programs is determined to be effective for a patient currently being treated with radiation for prostate cancer who has historically had high activity levels but recently has reduced his exercise levels.

For each of the various permutations of symptom combinations, cancer types, and other factors, the server system 310 may identify examples from its data set that represent the same or similar combination of aspects. Then, with information about how users have progressed with different combinations of programs and levels active, the server system 310 can assign likelihood scores indicating, for example, a probability that each level of each program is to achieve a desired result, such as reduction of a symptom or other outcome. The same analysis may be done to determine scores for different combinations of programs and levels. These likelihood scores may be used directly by the program state setting module 453. As another example, the likelihood scores may be assessed by the server system 310 to define rules that the program state setting module 453 applies to automatically initiate changes in program states.

In some implementations, the server system 310 may determine the specific set of factors experienced by an individual at a given time, and identify examples of users having the same or similar factors, based on databases of information maintained by the server system 310. The server system 310 may thus define, at various times, custom data sets from historical information about other users to determine a user specific likelihood of desired outcomes for the user's current situation. These user-specific measures may be used by the program state setting module 253, along with user-specific risk levels discussed above, to adjust program states.

In addition to or instead of using the centralized program state setting module 453, the rules of each program set the state of the program or another program. For example, program 4 may include rules that adjust the level of program for based on the input data to the program, which may indicate historical information about the user. Program 4 may also provide a signal to program 1 indicating that a level of program 1 should be changed. Alternatively, the level of program 4, or outputs to be provided to the user from program 4, maybe provided as input to program 1 and used to adjust program 1 according to program 1's own rules.

In some implementations, the records can include pharmacogenomics data from individual users. This information can allow cancer medications and related medications to be cross-referenced with the patient's genetic data. The server system 110 can use this information to estimate how medications have affected or will affect a user. For example, the server system 310 can perform an analysis of a patient's genetic profile to identify genes that affect the metabolism of specific medications. For example, there one set of genes may regulate medication metabolism in the liver, and variations in those genes may result in different metabolism rates for different individuals. Having identified genes that affect how a medication is processed by a user, the server system 310 can use the information to predict which medications may have adverse effects, may have stronger or weaker effects than expected, and so on. These results can be provided as a notice or warning to a user, family member or friend, caregiver or other health service provider, pharmacist, or other person. Similarly, the information can be provided to the digital therapeutics programs to provide current interventions. For example, if a user's genetic profile indicates genes that would cause a currently prescribed drug to metabolize in a manner that causes increased drowsiness, the corresponding scores for that side effect can be increased (with respect to probability and/or severity) for that particular user. Similarly, since the increased side effect risk may be a discouragement to actually taking the medication, the system 310 may determine that an additional level increase for a medication compliance program is appropriate, or that a caregiver should be notified to be more specifically verify that the medication is properly taken.

In some implementations, user pharmacogenomics data can also be used to identify or verify relationships between specific genetic features and effects of medications. For example, given the self-reported assessment results for pain, mood, and other characteristics, as well as activity levels detected with sensor data and confirming messages from caregivers and friends and family, the system 310 can identify correlations among specific genetic features, or combinations of genetic features, and certain effects of medications. This information may be used to update the medication database to provide scores for effect probability and intensity that are more specific for people with certain genetic profiles than for the population as a whole. As a result, in some implementations, the relationships between genetic features of individuals and likely effects of medication need not be predetermined, and can be learned and adjusted dynamically by the system over time through the analysis of changes in user survey results and monitored actions.

Figure 8:
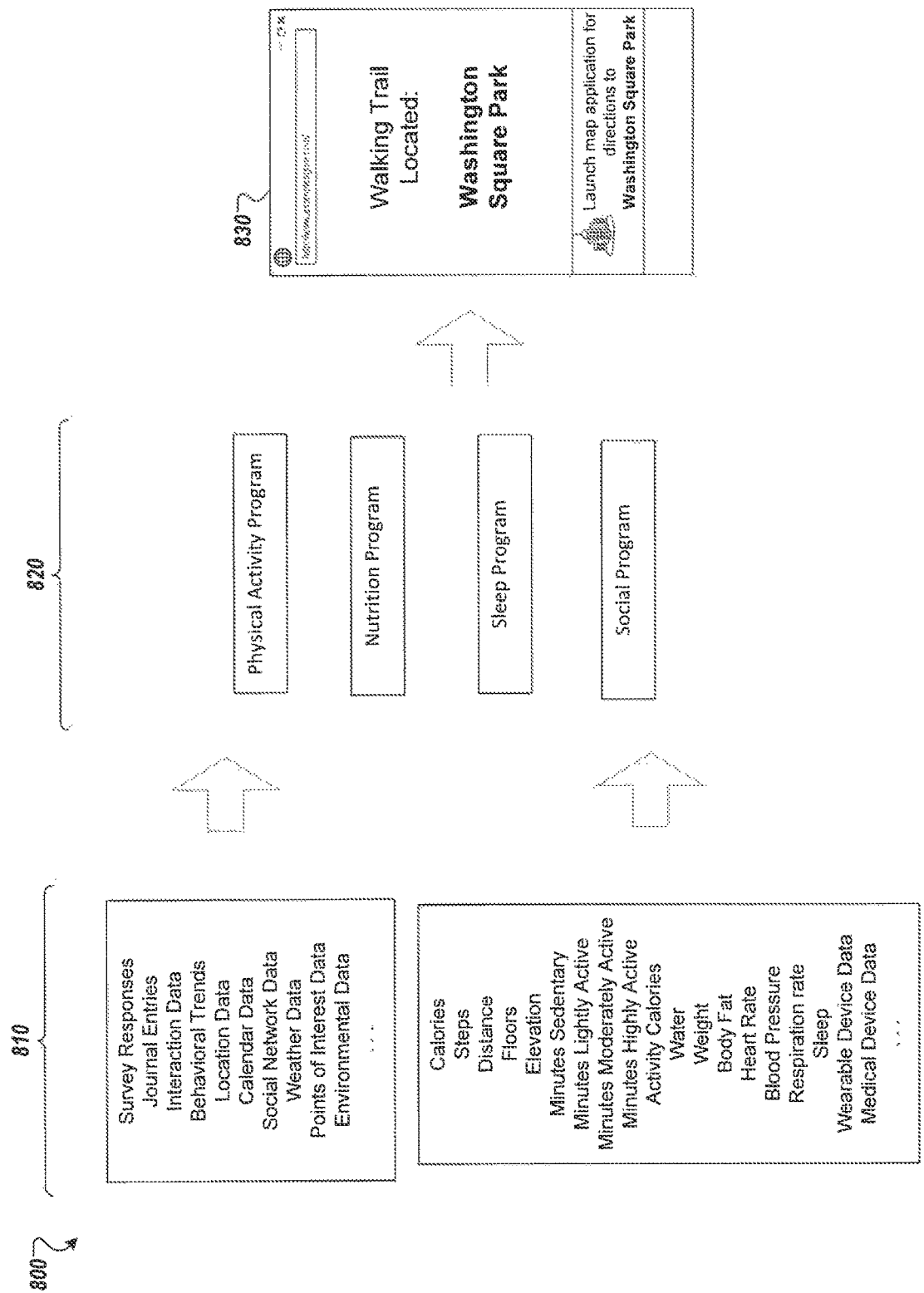
FIG. 8 is a diagram that illustrates examples of data that can be used by various operating plan programs for devices in complex systems.

FIG. 8 illustrates additional examples of data that can be used by various management programs, such as management programs used to change the operation of a device to support the health and wellbeing of a user of the device.

As illustrated, the server system 310 may receive various types of input data 810 such as survey responses, journal entries, interaction data, behavioral trends, location data, calendar data, social network data, electronic health records, prescription/medication data, genetic data, and other information about a user. Other input data 810 may represent general information, which may not be specific to a user can include weather data, points of interest data, environmental data, and so on. The types of data about a user that may be tracked include calories consumed, steps taken, distance walked, floors walked, elevation, minutes sedentary, minutes lightly active, minutes moderately active, minutes highly active, calories used during physical activity, water consumption, weight, body fat, heart rate, blood pressure, respiration rate, sleep times and amounts, glucose levels, wearable device data, medical device data, and so on.

A number of digital operating programs 820 are shown as examples. These programs may each have their own sets of content and rules that govern how they interact with users. Each program may be activated and deactivated separately to support a different aspect of a user's activities. Nevertheless, as discussed above, the levels or states of the programs may be adjusted based on the outputs and states of other programs to respond to a user's situation and to proactively provide support for expected challenges. In the illustration, separate programs are shown for goal setting, habit maintenance, and schedule management. Each of these programs may use any and all of the inputs to the server system 310 to determine how to interact with a user. The specific subset of programs that is active in a user's management plan at a given time, with the active segments and levels of those programs, is used to process the input data 810 and provide a customized management plan and interactive user interfaces 830.

While the techniques discussed herein are well-suited to serving cancer patients and cancer survivors, the same techniques can also be applied to provide digital therapeutics and improve wellness in other people also. For example, people who have a chronic physical condition, such as arthritis, diabetes, hepatitis, heart disease, COPD, etc., can also benefit from the application of various digital therapeutics programs and the analysis and adjustment in programs that the system provides. Similarly, the system may be used to treat and support users with psychological conditions such as depression, anxiety disorder, attention-deficit/hyperactivity disorder, bipolar disorder, etc. To assists these users, and any of the other types of users, the system may use cognitive behavioral therapy techniques to assist the users in adjusting behaviors, mood, etc. As another example, the system can be used to treat and support users recovering from a discrete event, such as surgery or trauma, e.g., a broken bone, a joint replacement, cataract surgery, and so on. As another example, the system may be used to support users in achieving general health, e.g., physical and/or psychological wellbeing. The system can encourage and guide users to improve or maintain a lifestyle on a day-to-day, or even moment-to-moment basis, as the various digital therapeutics programs determine are appropriate for the user given the current situation. As an example, programs for nutrition and physical fitness can prompt users to take incremental steps to reach goals that are set by the user or by the system. For all of these potential uses of the system and the different types of users, the ability for various digital therapeutics programs to interact and dynamically set their can provide improved responsiveness and efficiency of the system. Accordingly, in some implementations, the system can be used with different types of users who are not cancer patients or cancer survivors.

As discussed above, the states of different programs can be dynamically adjusted, based on current information about a user, historical information about the user, and based on the states of other programs. In addition, the types of interconnections between programs, e.g., the rules that define transitions between program states can also dynamically updated based on various factors. For example, the system can use information about the progress of users over time can be used to identify conditions or triggers that should cause state transitions. Groups of users that have certain commonalities can be identified and their progress assessed to determine these conditions and triggers, and which actions to perform, e.g., which programs to activate or deactivate, and which levels (e.g., program states) are most effective. In addition to or instead of using data about users of the system, population-level data can be used in a similar manner to determine which combinations of programs and interventions are appropriate for different users. The population-level data may represent information about a population of a city, county, state or province, country, continent, or the world. Combining information from the data sets of users of the system with population-level data can provide increased accuracy of predictions, better enabling the system to identify predicted interactions and interventions that will address the user's current or expected needs.

Figure 9:
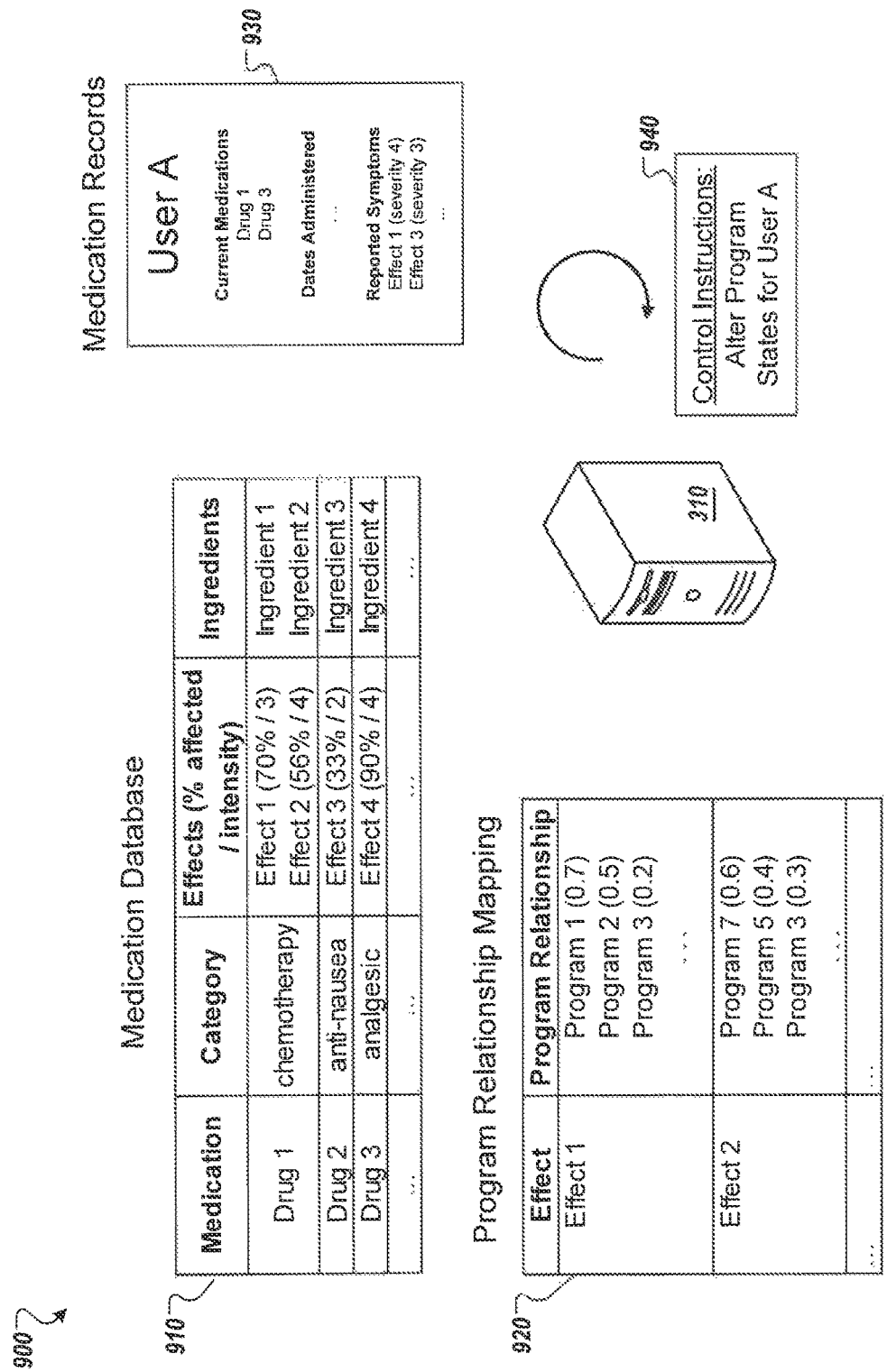
FIG. 9 is a diagram that illustrates examples of using medication information.

FIG. 9 is a diagram that illustrates examples of using medication information. The server system 310 can store information about various pharmaceuticals, as illustrated by medication database 910. As examples, medications can be indicated by an identifier and other information such as a name, category or type, manufacturer, manufacturing lot, etc. For each medication, effects of the medication (potentially both desired and undesired effects) can be specified as well as a list of ingredients, relative or absolute measures of amounts of the ingredients, and other information. The information about effects of the medications can indicate various scores, such as a likelihood score that a person taking the medication will experience the effect or a percentage indicating what percentage of people taking the medication experience the effect. Scores indicating the severity of the effect, e.g., an average measure for those who do experience the effect, can also be indicated The server system 310 can also store a mapping 920 indicating relationships between the effects of medications and different programs. For example, for a given medication effect, scores may be provided indicating a degree of relevance to different programs. The score may represent a relevance of the program or a degree to which the program can address the effect. For example, if the medication effect is insomnia, a sleep disorder program may have a high score in the mapping, since it includes content and interventions that can reduce the effect of that symptom. Similarly, a program for physical exercise or anxiety may have a score in the mapping that indicates a moderate relevance, since those programs may help also but to a lesser degree. The scores in the mapping 920 do not need to be based on intuitive relationships, however, and may be determined through analysis of clinical data tracked over time or through historical outcomes of users of the system. The scores may be manually defined in some instances.

The server system 310 also stores medication records 930 for each user. These records 930 can indicate current medications of the user as well as historical information about medications of the user. The records 930 can indicate a variety of metadata or contextual information about how and when the medications were administered, such as dates, times, doses, whether taken with food, form (e.g., patch, pill, injection, etc.), indication of prescribed usage (e.g., allowing the system to determine whether actual use corresponds with prescribed use), and so on. In addition, actual symptoms, side effects, or beneficial effects that the user experienced can be specified, as reported by the user directly through a mobile device, or through medical records or doctors assessments.

From the medication records 930 and other user data, the server system 310 can learn the appropriate mappings 920 and effects of medications. For example, with the data collected and assessed by the server system 310, previously unknown side effects or benefits of certain medications or combinations of medications can be discovered. Similarly, long-term effects of medications can be more accurately characterized and predicted. For example, the chemotherapy medications that a user took a year or two ago may contribute to ongoing or even later-arising symptoms. Even before these relationships are widely known or clinically proven, the server system 310 can identify these effects and characterize them in the medication database 910, e.g., with risk levels, typical severity, and factors contributing to increased risk. The mappings 920 can then indicate, for those effects, which program or combinations of programs are most effective in assisting a user to deal with the effects.

Using the user's medication records 930, and the indications of which medications were taken when, the server system 310 can look up in the medication database 910 which medication effects are likely for the user. In addition, the server system 310 can use the mapping 920 to determine which programs (and potentially specific levels and segments of the programs) are most relevant to the likely effects. Given a likely effect predicted using the medication records, or from actual effects indicated by the medication records, the server system 310 identifies the relevance scores for one or more programs. The server system 310 may then combine the scores across different effects.

For example, all effects of current medications of a user and former medications of a user can be determined. The scores in the mapping 920 are determined for each of these effects. Then, for each program, the relevance scores may be combined by weighting the values. Scores corresponding to likely effects may be weighted or discounted according to the likelihood from the medication database 910. Similarly, scores for effects estimated from medications that are not current may be discounted in some instances based on how long ago the corresponding medication was administered. Similarly, scores can be weighted by the typical intensity of the effect. By contrast, for actual effects experienced by the user, the scores from the mapping 920 may not be discounted, or may be increased. The weighted scores for a program may then be added or otherwise combined to give an overall measure of the likely relevance of the program to the user given the user's current medications and medication history. The combined scores for the program are then compared to a threshold, and if the score satisfies the threshold, the corresponding program may be activated or have its level increased. The same technique can be used for each of the programs available.

With these techniques, the system 310 can activate digital therapeutics programs to address the actual effects experienced by a patient. The system 310 can also activate programs to address potential effects that may be likely but may not be reported by a patient or may be developed in the future. The server system 310 can generate control instructions 940 that specify specific programs to activate, deactivate, or change in level based on the analysis of the user's medication records 930, and based on the other information discussed above.

In some implementations, the records can include pharmacogenomics data from individual users. This information can allow cancer medications and related medications to be cross-referenced with the patient's genetic data. The server system 310 can use this information to estimate how medications have affected or will affect a user. For example, the server system 310 can perform an analysis of a patient's genetic profile to identify genes that affect the metabolism of specific medications. For example, there one set of genes may regulate medication metabolism in the liver, and variations in those genes may result in different metabolism rates for different individuals. Having identified genes that affect how a medication is processed by a user, the server system 310 can use the information to predict which medications may have adverse effects, may have stronger or weaker effects than expected, and so on. These results can be provided as a notice or warning to a user, family member or friend, caregiver or other health service provider, pharmacist, or other person. Similarly, the information can be provided to the digital therapeutics programs to provide current interventions. For example, if a user's genetic profile indicates genes that would cause a currently prescribed drug to metabolize in a manner that causes increased drowsiness, the corresponding scores for that side effect can be increased (with respect to probability and/or severity) for that particular user. Similarly, since the increased side effect risk may be a discouragement to actually taking the medication, the system 310 may determine that an additional level increase for a medication compliance program is appropriate, or that a caregiver should be notified to be more specifically verify that the medication is properly taken.

In some implementations, user pharmacogenomics data can also be used to identify or verify relationships between specific genetic features and effects of medications. For example, given the self-reported assessment results for pain, mood, and other characteristics, as well as activity levels detected with sensor data and confirming messages from caregivers and friends and family, the system 310 can identify correlations among specific genetic features, or combinations of genetic features, and certain effects of medications. This information may be used to update the medication database to provide scores for effect probability and intensity that are more specific for people with certain genetic profiles than for the population as a whole. As a result, in some implementations, the relationships between genetic features of individuals and likely effects of medication need not be predetermined, and can be learned and adjusted dynamically by the system over time through the analysis of changes in user survey results and monitored actions.

Embodiments of the invention and all of the functional operations described in this specification may be implemented in digital electronic circuitry, or in computer software, firmware, or hardware, including the structures disclosed in this specification and their structural equivalents, or in combinations of one or more of them. Embodiments of the invention may be implemented as one or more computer program products, i.e., one or more modules of computer program instructions encoded on a computer-readable medium for execution by, or to control the operation of, data processing apparatus. The computer readable medium may be a non-transitory computer readable storage medium, a device-readable storage device, a device-readable storage substrate, a memory device, a composition of matter effecting a device-readable propagated signal, or a combination of one or more of them. The term "data processing apparatus" encompasses all apparatus, devices, and devices for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a device-generated electrical, optical, or electromagnetic signal that is generated to encode information for transmission to suitable receiver apparatus.

A computer program (also known as a program, software, software application, script, or code) may be written in any form of programming language, including compiled or interpreted languages, and it may be deployed in any form, including as a stand-alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media, and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, embodiments of the invention may be implemented on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any form of sensory feedback, e.g., visual feedback, auditory feedback, or tactile feedback; and input from the user may be received in any form, including acoustic, speech, or tactile input.

Embodiments of the invention may be implemented in a computing system that includes a back end component, e.g., as a data server, or that includes a middleware component, e.g., an application server, or that includes a front end component, e.g., a client computer having a graphical user interface or a Web browser through which a user may interact with an implementation of the invention, or any combination of one or more such back end, middleware, or front end components. The components of the system may be interconnected by any form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Thus, particular embodiments of the invention have been described. Other embodiments are within the scope of the following claims. For example, the actions recited in the claims may be performed in a different order and still achieve desirable results.

What is claimed is:

1. A method performed by one or more computers, the method comprising:
   obtaining, by the one or more computers, (i) status data indicating digital therapeutics program settings of digital therapeutics programs provided to a set of multiple users using mobile computing devices, wherein at least some of the digital therapeutics program settings indicate which of the digital therapeutics programs have been used for the respective users in the set and (ii) user data indicating characteristics or outcomes for the users in the set;
   analyzing, by the one or more computers, the status data and the user data to determine relationships among (i) the digital therapeutics program settings assigned for the users and (ii) the characteristics or outcomes for the users, the analysis indicating that a particular one or more of the digital therapeutics program settings being assigned corresponds to an increased likelihood of a particular characteristic or outcome;
   based on the analysis, defining, by the one or more computers, a marker that represents an increased likelihood for the particular characteristic or outcome, wherein the marker is defined to be present when one or more conditions are met, the one or more conditions including the particular one or more of the digital therapeutics program settings having been assigned for an individual;
   determining, by the one or more computers, that the marker for the particular characteristic or outcome is present for a particular user based at least in part on determining that a set of digital therapeutics program settings that have been assigned for the particular user includes the particular one or more of the digital therapeutics settings; and
   based on determining that the marker for the particular characteristic or outcome is present for the particular user, causing, by the one or more computers, one or more interactions to be provided by a mobile computing device associated with the particular user, wherein the one or more interactions comprise initiating a measurement with a sensor, providing a survey, or providing content selected for the particular user.

2. The method of claim 1, wherein the digital therapeutics program settings are program states of the digital therapeutics programs.

3. The method of claim 1, wherein the marker is defined so that the one or more conditions include (i) the particular one or more of the digital therapeutics program settings being assigned and (ii) presence of at least one of a physical, genetic, behavioral, or health trait.

4. The method of claim 1, wherein causing the one or more interactions to be provided comprises providing, as input to one or more digital therapeutics programs, an indication that the marker is present, wherein the one or more digital therapeutics programs are configured to select the one or more interactions based at least in part on the indication that the marker is present.

5. The method of claim 1, wherein the one or more interactions comprise one or more interventions tailored to alter one or more behaviors of the particular user that cause the marker to be present.

6. The method of claim 1, wherein the marker is a marker for a health risk; and
   wherein the one or more interactions comprise one or more interventions to encourage one or more behaviors of the user that decrease the health risk associated with the marker.

7. The method of claim 1, wherein the marker is a marker for a health risk; and
   wherein the one or more interactions comprise adding a particular additional digital therapeutics program for the user to reduce a risk of a future complication associated with the particular characteristic or outcome.

8. The method of claim 1, comprising identifying, by the one or more computers, digital therapeutics interventions to improve health of users that have a risk of developing the particular characteristic or outcome.

9. The method of claim 8, wherein identifying the digital therapeutics interventions to improve health outcomes of users comprises:
   identifying, by the one or more computers, a group of the users that have a set of characteristics in common;

determining, by the one or more computers, changes in digital therapeutics program settings of the users in the group; and identifying, by the one or more computers and based on transitions between different sets of digital therapeutics program settings assigned for the users in the group, combinations of digital therapeutics settings applied for the users in the group that reduced symptoms of the users or changes in the digital therapeutics program settings that reduced symptoms of the users.

10. The method of claim 1, wherein the status data indicates different combinations of digital therapeutics program settings, wherein the different combinations were used to select interactions of digital therapeutics programs provided to different users of mobile computing devices;

wherein analyzing the status data and the user data comprises determining relationships among the combinations of the digital therapeutics program settings assigned for the users and the characteristics or outcomes for the users, the analysis indicating that a particular combination of the digital therapeutics program settings corresponds to an increased likelihood of a particular characteristic or outcome; and wherein the marker is defined to be present when the particular combination of the digital therapeutics program settings has been assigned for an individual.

11. The method of claim 1, wherein causing the one or more interactions to be provided by the mobile computing device associated with the particular user comprises changing, for the particular user, program states in a user-specific set of program states of one or more of the digital therapeutics programs based on determining that the marker for the particular characteristic or outcome is present.

12. The method of claim 1, wherein the one or more interactions comprise one or more interactions selected to improve health outcomes for users at risk for the particular characteristic or outcome.

13. The method of claim 1, wherein the digital therapeutics program settings comprise settings for the digital therapeutics programs that affect how corresponding digital therapeutics programs interact with a user.

14. The method of claim 1, wherein at least some of the digital therapeutics program settings specify different levels of intensity or interaction for the digital therapeutics programs.

15. The method of claim 1, comprising:
based on determining that the particular user exhibits the marker, altering, by the one or more computers, digital therapeutics program settings associated with the particular user to alter digital therapeutics provided to the particular user.

16. The method of claim 1, wherein defining the marker that represents an increased likelihood for the particular characteristic or outcome comprises defining the marker to represent a risk of a particular disease.

17. The method of claim 1, wherein the user data comprises data sets for longitudinal studies that include data collections describing many individuals, their characteristics, and their health outcomes over time; and wherein causing the one or more interactions to be provided comprises using the marker as an indicator for selecting a digital therapeutic for the particular user.

18. The method of claim 1, wherein the status data indicates digital therapeutics program settings were used to provide interactions of digital therapeutics programs to the respective users in the set of users through mobile computing devices;

wherein defining the marker comprises defining the marker to be a predictive marker for a health risk;

wherein determining that the marker is present comprises determining that the particular user exhibits the predictive marker for the health risk based on determining that the particular one or more of the digital therapeutics program settings have been assigned for the particular user; and wherein causing the one or more interactions to be provided comprises causing the mobile computing device associated with the particular user to provide digital therapeutics interactions for managing the health risk in response to detecting the predictive marker for the health risk.

19. A system comprising:
one or more computers; and
one or more computer-readable media storing instructions that, when executed by the one or more computers, cause the one or more computers to perform operations comprising:

obtaining, by the one or more computers, (i) status data indicating digital therapeutics program settings provided to a set of multiple users using mobile computing devices, wherein at least some of the digital therapeutics program settings indicate which of the digital therapeutics programs have been used for the respective users in the set and (ii) user data indicating characteristics or outcomes for the users in the set;

analyzing, by the one or more computers, the status data and the user data to determine relationships among (i) the digital therapeutics program settings assigned for the users and (ii) the characteristics or outcomes for the users, the analysis indicating that a particular one or more of the digital therapeutics program settings being assigned corresponds to an increased likelihood of a particular characteristic or outcome;

based on the analysis, defining, by the one or more computers, a marker that represents an increased likelihood for the particular characteristic or outcome, wherein the marker is defined to be present when one or more conditions are met one or more conditions including the particular one or more of the digital therapeutics program having been assigned for an individual;

determining, by the one or more computers, that the marker for the particular characteristic or outcome is present for a particular user based at least in part on determining that a set of digital therapeutics program settings that have been assigned for the particular user includes the particular one or more of the digital therapeutics settings; and based on determining that the marker for the particular characteristic or outcome is present for the particular user, causing, by the one or more computers, one or more interactions to be provided by a mobile computing device associated with the particular user, wherein the one or more interactions comprise initiating a measurement with a sensor, providing a survey, or providing content selected for the particular user.

20. The system of claim 19, wherein the digital therapeutics program settings are program states of the digital therapeutics programs.

21. The system of claim 19, wherein the marker is defined to be present for a user based on a combination of (i) the particular one or more of the digital therapeutics program settings being associated with the individual and (ii) at least one of a physical, genetic, behavioral, or health trait.

22. The system of claim 19, wherein causing the one or more interactions to be provided comprises providing, as input to one or more digital therapeutics programs, an indication that the marker is present, wherein the one or more digital therapeutics programs are configured to select the one or more interactions based at least in part on the indication that the marker is present.

23. The system of claim 19, wherein the one or more interactions comprise one or more interventions tailored to alter one or more behaviors of the particular user that cause the marker to be present.

24. One or more non-transitory computer-readable media storing instructions that, when executed by the one or more computers, cause the one or more computers to perform operations comprising:

obtaining, by the one or more computers, (i) status data indicating digital therapeutics program settings of digital therapeutics programs provided to a set of multiple users using mobile computing devices, wherein at least some of the digital therapeutics program settings indicate which of the digital therapeutics programs have been used for the respective users in the set and (ii) user data indicating characteristics or outcomes for the users in the set;

analyzing, by the one or more computers, the status data and the user data to determine relationships among (i) the digital therapeutics program settings assigned for the users and (ii) the characteristics or outcomes for the users, the analysis indicating that a particular one or more of the digital therapeutics program settings corresponds to an increased likelihood of a particular characteristic or outcome;

based on the analysis, defining, by the one or more computers, a marker that represents an increased likelihood for the particular characteristic or outcome, wherein the marker is defined to be present when one or more conditions are met, the one or more conditions including the particular one or more of the digital therapeutics program settings having been assigned for an individual;

determining, by the one or more computers, that the marker for the particular characteristic or outcome is present for a particular user based at least in part on determining that a set of digital therapeutics program settings that have been assigned for the particular user includes the particular one or more of the digital therapeutics settings; and based on determining that the marker for the particular characteristic or outcome is present for the particular user, causing, by the one or more computers, one or more interactions to be provided by a mobile computing device associated with the particular user, wherein he one or more interactions comprise initiating a measurement with a sensor, providing a survey, or providing content selected for the particular user.

25. The one or more non-transitory computer-readable media of claim 24, wherein the digital therapeutics program settings are parameters that each represent a state or configuration of a corresponding digital therapeutics program.

* * * * *

UNITED STATES PATENT AND TRADEMARK OFFICE
CERTIFICATE OF CORRECTION

PATENT NO. : 11,153,159 B2  
APPLICATION NO. : 16/711506  
DATED : October 19, 2021  
INVENTOR(S) : Jain et al.

Page 1 of 1

It is certified that error appears in the above-identified patent and that said Letters Patent is hereby corrected as shown below:

In the Claims

Column 50, Line 41 in Claim 19, delete "met" and insert -- met, the --, therefor.

Column 50, Line 43 in Claim 19, after "program" insert -- settings --.

Column 52, Line 23 in Claim 24, delete "he" and insert -- the --, therefor.

Signed and Sealed this  
Fourth Day of January, 2022

Drew Hirshfeld  
*Performing the Functions and Duties of the*  
*Under Secretary of Commerce for Intellectual Property and*  
*Director of the United States Patent and Trademark Office*